(12) United States Patent
Kerwin et al.

(10) Patent No.: US 6,623,930 B2
(45) Date of Patent: Sep. 23, 2003

(54) INHIBITION OF HUMAN TELOMERASE BY A G-QUADRUPLEX-INTERACTION COMPOUND

(75) Inventors: Sean M. Kerwin, Round Rock, TX (US); Oleg Y. Fedoroff, Austin, TX (US); Miguel Salazar, Katy, TX (US); Laurence H. Hurley, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 145 days.

(21) Appl. No.: 09/940,173

(22) Filed: Aug. 27, 2001

(65) Prior Publication Data

US 2003/0040525 A1 Feb. 27, 2003

Related U.S. Application Data

(62) Division of application No. 09/730,893, filed on Dec. 5, 2000, which is a division of application No. 09/244,675, filed on Feb. 4, 1999, now Pat. No. 6,156,763.
(60) Provisional application No. 60/073,629, filed on Feb. 4, 1998.

(51) Int. Cl.[7] .......................... C12Q 1/68; A61K 31/44; C07D 21/22
(52) U.S. Cl. .............................. 435/6; 514/279; 546/37

(56) References Cited

U.S. PATENT DOCUMENTS 6,087,493 A * 7/2000 Wheelhouse et al.
6,156,763 A * 12/2000 Kerwin et al.
6,492,117 B1 * 12/2002 Choo et al.
6,528,517 B1 * 3/2003 Hurley et al.

OTHER PUBLICATIONS

Agbandje et al., "Anthracene-9,10-diones as potential anti-cancer agents. Synthesis, DNA binding, and biological studies on a series of 2,6-disubstituted derivatives," Med. Chem., 35:1418–1429, 1992.
Broccoli et al., "Telomerase activity in normal and malignant hematopoietic cells," Proc. Natl. Acad. Sci. U.S.A, 92:9082–9086, 1995.
Chen et al., "Spectroscopic recognition of guanine dimeric hairpin quadruplexes by a carbocyanine dye," Proc. Natl. Acad. Sci. U.S.A., 93:2635–2639, 1996.
Chung et al., "p-Quinone methides as geometric analogues of quinolone carboxylate antibacterials," Bioorganic & Medicinal Chem. Letters, 6(12):1309–1312, 1996.
Collier et al., "Synthesis, molecular modeling DNA binding, and antitumor properties of some substituted amidoanthraquinones," Med. Chem., 31:847–857, 1988.
Ebisuno et al., "The cytotoxic effects of fleroxacin and ciprofloxacin on transitional cell carcinoma in vitro," Cancer, 80(12):2263–2267, 1997.
Fedoroff et al., "NMR-based model of a telomerase–inhibiting compound bound to G–quadruplex DNA," Biochemistry, 37(36):12367–12374, 1998.
Fox et al., "A molecular anchor for stabilizing triple–helical DNA," Proc. Natl. Acad. Sci. U.S.A., 92:7887–7891, 1995.
Greider et al., "Identification of a specific telomere terminal transferase activity in Tetrahymena extracts," Cell, 43(2Ptl):405–413, 1995.
Haq et al., "Molecular anchoring of duplex and triplex DNA by disubstituted anthracene–9/10–diones: calorimetric, UV melting, and competition dialysis studies," J. Am. Chem. Soc., 118:10693–10701, 1996.
Hertzberg and Johnson, "Antineoplastic Agents," In: Annual Reports in Medicinal Chemistry, Plattner (ed.) 18:167–176, 1993.
Hsiung et al., "A mutation in yeast TOP2 homologous to a quinolone–resistant mutation in bacteria," The J. of Biol. Chem., 270(35):20359–20364, 1995.
Izbicka et al., "Effects of cationic porphyrins as G–quadruplex interactive agents in human tumor cells," Cancer Res, 59(3):639–644, 1999.
Khac and Moreau, "Interactions between fluoroquinolones, $Mg^{2+}$, DNA and DNA gyrase, studied by phase partitioning in an aqueous two–phase system and by affinity chromatography," J. of Chromatography A, 668:241–247, 1994.
Kim et al., "Specific association of human telomerase activity with immortal cells and cancer," Science, 266:2011–2015, 1994.
Laughlan et al., "The high–resolution crystal structure of a parallel–stranded guanine tetraplex," Science, 265:520–524, 1994.
Lecomte et al., NMR investigation of pefloxacin–cation–DNA interactions: the essential role of $Mg^{2+}$, Intl. J. of Pharmaceutics, 164:57–65, 1998.
Lecomte and Chenon, "NMR investigation of pefloxacin/cation/DNA interactions. $Mg^{2+}$ and $Ca^{2+}$ Binding," Intl. J. of Pharmaceutics, 139:105–112, 1996.
Lecomte et al., "Effect of magnesium complexation by fluoroquinolones on their antibacterial properties," Antimicrobial Agents and Chemotherapy, 38(12):2810–2816, 1994.

(List continued on next page.)

Primary Examiner—Ethan Whisenant
(74) Attorney, Agent, or Firm—Fulbright & Jaworski

(57) ABSTRACT

Certain non-nucleoside compounds that will selectively inhibit telomerase by targeting the nucleic add structures, such as G-quadruplexes, that may be associated with human telomeres or telomerase have been identified. Inhibition of human telomerase by two perylenetetracarboxylic acid diimides and a carbocyanine has been demonstrated. $^1$H-NMR studies have evidenced the stabilization of a G-quadruplex by the perylenetetracarboxylic acid diimide compounds and provided evidence that these and structurally related compounds inhibit the telomerase enzyme by a mechanism consistent with interaction with G-quadruplex structures.

1 Claim, 11 Drawing Sheets

OTHER PUBLICATIONS

Lecomte et al., "NMR investigation of pefloxacin–cation–DNA interactions," 1995.

Llorente et al., "Using SAR and QSAR analysis to model the activity and structure of the quinolone–DNA complex," *Bioorganic & Medicinal Chem.*, 4(1):61–71, 1996.

Martinez et al., "Effect of magnesium and calcium complexation on the photochemical properties of norfloxacin," *Photochemistry and Photobiology*, 64(6):911–917, 1996.

Norton et al., "Inhibition of human telomerase activity by peptide nucleic acids," *Nature Biotechnology*, 14:615–619, 1996.

Palmer et al., "Potential antitumor agents. 54. Chromophore requirements for in vivo antitumor activity among the general class of linear tricyclic carboxamides," *J. Med. Chem.*, 31:707–712, 1988.

Parkinson, "Do telomerase antagonists represent a novel anti–cancer strategy?" *Brit. J. Cancer*, 73:1–4, 1996.

Perry et al., "1,4–and 2,6–disubstituted amidoanthracene–9,10–dione derivatives as inhibitors of human telomerase," *J Med. Chem.*, 41(17):3252–3260, 1998.

Perry et al., "Human telomerase inhibition by regioisomeric disubstituted amidoanthracene–9,10–diones," Abstract, *J. Med. Chem.*, 41(24):4873–4884, 1998.

Rodighiero et al., "Angular furoquinolinones, psoralen analogs: novel antiproliferative agents for skin diseases. Synthesis, biological activity, mechanism of action, and computer–aided studies," *J. Med. Chem.*, 39:1293–1302, 1996.

Ross and Riley, "Physicochemical properties of the fluoroquinolone antimicrobials. III. Complexation of lomefloxacin with various metal ions and the effect of metal ion complexation on aqueous solubility," *Int. J. of Pharmaceutics*, 87:203–213, 1992.

Ross and Riley, "Physicochemical properties of the fluoroquinolone antimicrobials. II. Acid ionization constants and their relationship to structure," *Intl. J. of Pharmaceutics*, 83:267–272, 1992.

Salazar et al., "Thermally induced DNA:RNA hybrid to G–quadruplex transitions: possible implications for telomere synthesis by telomerase," *Biochemistry*, 35:16110–16115, 1996.

Sen and Gilbert, "A sodium–potassium switch in the formation of four–stranded G4–DNA," *Nature*, 344(6265):410–414, 1990.

Sun et al., "Inhibition of human telomerase by a G–quadruplex–interactive compound," *M. Med. Chem.*, 40(14):2113–2116, 1997.

Tanious et al., "Substituent position dictates the intercalative DNA–binding mode for anthracene–9,10–dione antitumor drugs," *Biochemistry*, 31:11632–11640, 1992.

Wang et al., "Guanine residues in $d(T_2AG_3)$ and $(T_2G_4)$ form parallel–stranded potassium cation stabilized G–quadruplexes with anti glycosidic torsion angles in solution," *Biochemistry*, 31:8112–8119, 1992.

Weitzmann et al., "The development and use of a DNA polymerase arrest assay for the evaluation of parameters affecting intrastrand tetraplex formation," *J. Biol. Chem.*, 271(34), 20958–20964, 1996.

Wentland et al., "Mammalian topoisomerase II inhibitory activity of 1–cyclopropyl–6,8–difluoro–1,4–dihydro–7–(2,6–dimethyl–4–pyridinyl)–4–oxo–3–quinolinecarboxylic acid and related derivatives," *J. Med. Chem.*, 36:2801–2809, 1993.

Yamakuchi et al., "New quinolones, ofloxacin and levofloxacin, inhibit telomerase activity in transitional cell carcinoma cell lines," Abstract, *Cancer Letters*, 119(2):213–219, 1997.

Zahler et al., "Inhibition of telomerase by G–quartet DNA structures," *Nature*, 350:718–720, 1991.

Grootenhuis et al., "Finding potential DNA–binding compounds by using molecular shape," Abstract, *J. Comput. Aided Mol. Des.*, 8(6):731–750, Dec., 1994.

Kaufman and Hancock, "Topoisomerase II as a target for anticancer chemotherapy," Abstract, *Acta Biochem. Pol.*, 42(4):381–393, 1995.

\* cited by examiner

G4A: 5'CATGGTGGTTTGGGTTAGGGTTAGGGTTAGGGTTACCAC3'
        1 2 3      4 5 6    7 8 9   10 11 12

Intramolecular Quadruplex DNA

SEQUENCE LISTING

```
<160> NUMBER OF SEQ ID NOS: 12

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1 ttaggg                                                                    6

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
```

```
agggttaggg ttagggttag gg                                              22

<210> SEQ ID NO 3
<211> LENGTH: 7
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3 taagggt                                                                7

<210> SEQ ID NO 4
<211> LENGTH: 8
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4 ttagggtt                                                               8

<210> SEQ ID NO 5
<211> LENGTH: 7
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5 aatgggt                                                                7

<210> SEQ ID NO 6
<211> LENGTH: 7
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6 ttagggt                                                                7

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7 ttgggg                                                                 6

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
```

```
agggttaggg ttagggttag gg                                        22

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9
taatacgact cactatag                                             18

<210> SEQ ID NO 10
<211> LENGTH: 80
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
tccaactatg tatacttggg gttgggttg gggttggggt tggggttagc ggcacgcaat 60
tgctatagtg agtcgtatta                                           80

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
catggtggtt tgggttaggg ttagggttag ggttaccac                      39

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12
taatacgact cactatag                                             18
```

INHIBITION OF HUMAN TELOMERASE BY A G-QUADRUPLEX-INTERACTION COMPOUND

The present application is a division of copending U.S. application Ser. No. 09/730,893, filed Dec. 5, 2000, which is a division of U.S. application Ser. No. 09/244,675, filed Feb. 4, 1999, and now issued as U.S. Pat. No. 6,156,763, which claims the priority of U.S. Provisional Patent Application Serial No. 60/073,629, filed Feb. 4, 1998. The entire disclosure of each of these applications is incorporated herein by reference without disclaimer.

The government may own rights in the present invention pursuant to contract number U19CA-67760-02, and contract number NCDDG, CA67760 from the National Cancer Institute, and contract number CA49751 and contract number CA77000 from the National Institutes of Health.

BACKGROUND OF THE INVENTION

I. Field of the Invention

This invention relates to the field of cancer therapy. The invention also relates to screening methods for identifying pharmacologically active compounds that may be useful for treating proliferative diseases. More particularly, the inventors have identified non-nucleoside molecule compounds that interact with specific DNA structures and which inhibit human telomerase.

II. Description of Related Art

Cancer, which is a cell proliferative disorder, is one of the leading causes of disease, being responsible for 526,000 deaths in the United States each year (Boring et al., 1993). For example, breast cancer is the most common form of malignant disease among women in Western countries and, in the United States, is the most common cause of death among women between 40 and 55 years of age (Forrest, 1990). The incidence of breast cancer is increasing, especially in older women, but the cause of this increase is unknown. Malignant melanoma is another form of cancer whose incidence is increasing at a frightening rate, at least sixfold in the United States since 1945, and is the single most deadly of all skin diseases (Fitzpatrick, 1986).

One of the devastating aspects of cancer is the propensity of cells from malignant neoplasms which disseminate from their primary site to distant organs and develop into metastatic cancers. Animal tests indicate that about 0.01% of circulating cancer cells from solid tumors establish successful metastatic colonies (Fidler, 1993). Despite advances in surgical treatment of primary neoplasms and aggressive therapies, most cancer patients die as a result of metastatic disease. Hence, there is a need for new and more efficacious cures for cancer.

The ends of chromosomes have specialized sequences, termed telomeres, comprising tandem repeats of simple DNA sequences. Human telomeres consist of the sequence 5'-TTAGGG (SEQ ID No. 1) (Blackburn, 1991; Blackburn et al., 1995). Telomeres have several functions apart from protecting the ends of chromosomes, the most important of which appear to be associated with senescence, replication, and the cell cycle clock (Counter et al., 1992). Progressive rounds of cell division result in a shortening of the telomeres by some 50–200 nucleotides per round. Almost all tumor cells have shortened telomeres, which are maintained at a constant length (Allshire et al., 1988; Harley et al., 1990; Harley et al., 1994) and are associated with chromosome instability and cell immortalization.

The enzyme telomerase adds the telomeric repeat sequences onto telomere ends, ensuring the net maintenance of telomere length in tumor cells commensurate with successive rounds of cell division. Telomerase is a DNA polymerase with an endogenous RNA template (Feng et al., 1995), on which the nascent telomeric repeats are synthesized. A significant recent finding has been that approximately 85–90% of all human cancers are positive for telomerase, both in cultured tumor cells and primary tumor tissue, whereas most somatic cells appear to lack detectable levels of telomerase (Kim et al., 1994; Hiyama et al., 1995a). This finding has been extended to a wide range of human tumors (see, for example, references Broccoli, 1994 and Hiyama et al., 1995b) and is likely to be of use in diagnosis.

Human telomerase has been proposed as a novel and potentially highly selective target for antitumor drug design (Feng et al., 1995; Rhyu et al., 1995; Parkinson, 1996). Studies with antisense constructs against telomerase RNA in HeLa cells show that telomere shortening is produced, together with the death of these otherwise immortal cells (Feng et al., 1995). Sequence-specific peptide-nucleic acids directed against telomerase RNA have also been found to exert an inhibitory effect on the enzyme Norton et al, 1996).

Among chemical agents, 2,6-diamido-anthraquinones have been reported as DNA-interactive agents (Collier and Neidle, 1988; 1992; Agbandje et al., 1992). These compounds have been shown to act as selective DNA triplex interactive compounds (Fox et al., 1995; Haq et al., 1996), with reduced affinity for duplex DNA and only moderate conventional cytotoxicity in a range of tumor cell lines. A carbocyanine dye, 3,3'-diethyloxadicarbocyanine (DODC,), has been reported to bind dimeric hairpin G-quadruplex structures (Chen et al., 1996).

This invention describes a novel class of non-nucleoside molecules that are telomerase inhibitors. These compounds have demonstrated their ability to interact with telomeres which form structures called the G-quadruplex structures. As telomeres are involved in controlling the cell cycle, cell replication and aging, these inhibitors of telomerase prevent uncontrolled cell growth and the immortality of tumor cells.

SUMMARY OF THE INVENTION

The present invention has demonstrated for the first time that a non-nucleoside, small molecule can target the G-quadruplex structure and can act as a telomerase inhibitor. Accordingly, methods have been developed that identify these classes of compounds and several inhibitors identified.

Compounds such as those described here, which interact selectively with G-quadruplex structures and inhibit telomerase, are expected to be useful as inhibitors of the proliferation of cells that require telomerase to maintain telomere length for continued growth. The invention thus relates to novel methods for identifying compounds that will be useful in this regard, and also includes new classes of telomerase inhibitors. In this regard, several perylene compounds and carbocyanines have been shown to interact with G-quadruplex structures. Since telomerase appears to be found almost exclusively in tumor cells, these agents are contemplated to be useful as antitumor agents.

In one aspect of the invention, compounds that act as telomerase inhibitors have been identified. It has been found that compounds that bind to the human G-quadruplex structure inhibit the human telomerase. The identification of such G-quadruplex interactive agents is an efficient approach for identifying human telomerase inhibitors. Methods for identifying these G-quadruplex interactive agents include identifying compounds whose three-dimensional structure is complementary to that of the G-quadruplex structure.

Another method for identifying G-quadruplex interactive compounds is to identify compounds that interact with G-quadruplexes using such methods as dye displacement or melting points of G-quadruplex/compound hybrids.

More particularly, candidate compounds that inhibit telomerase activity are identified by first obtaining the three-dimensional structure of a compound that might interact with the G-quadruplex.selected compound. The complementarity of the compound to human telomere DNA G-quadruplex is then determined. If there is a high degree of complementarity, telomerase inhibition activity is indicated.

Alternatively, one can contact a telomerase inhibitor candidate compound with human DNA G-quadruplex; and then determine the melting point of the human DNA G-quadruplex. The inventors have found that an increase in melting point of the quadruplex indicates telomerase inhibitory activity of the compound.

Additionally, telomerase inhibitors may be identified by first preparing a DNA G-quadruplex/dye complex with a dye intercalated into the G-quadruplex; then contacting complex with a telomerase inhibitor candidate. Displacement of the dye in the complex identifies the candidate as a telomerase inhibitor.

Yet another aspect of this invention is to provide non-nucleoside inhibitors of telomerase. Using the disclosed screening methods, compounds have been identified that bind to human G-quadruplex structures. The invention includes perylene compounds, exemplified by N,N'-bis(2-dimethylaminoethyl)-3,4,9,10-perylenetetracarboxylic acid diimide that are useful telomerase inhibitors. Novel compounds such as N,N'-bis(2-piperdinoethyl)-3,4,9,10-perylenetetracarboxylic acid diimide are also within the scope of the invention.

A preferred G-quadruplex structure is formed from the sequence d(AGGGTTAGGGTTAGGGTTAGGG) (SEQ ID No. 2) or the sequences d(TTAGGG)$_4$ (SEQ ID No. 1), d(TAAGGGT)$_4$ (SEQ ID No. 3), or d(TTAGGGTT)$_4$ (SEQ ID No. 4) either alone or in the presence of a G-quadruplex interactive perylene diimide of general structure I. The structures were determined by NMR spectroscopy. Alternatively, one may determine the three-dimensional structure of potential G-quadruplex interactive agents by x-ray diffraction or molecular mechanics calculations. Preferred programs for determining the degree of complementarity between the potential G-quadruplex interactive agent and these G-quadruplex structures include DOCK, autoDOCK, AMBER and SYBYL. The preferred methods for generating orientations between the potential G-quadruplex interactive agents and these G-quadruplex structures are manual and using the DOCK or autoDOCK programs. The cutoff for determining the likelihood that the orientation of the potential G-quadruplex interactive agent and the G-quadruplex structure have sufficient chemical interaction to form a complex is roughly 75% of the favorable intermolecular interaction energy, calculated with the above programs, of the perylene diimide 2-d(TTAGGG)$_4$ (SEQ ID No. 1) complex structure as determined by NMR spectroscopy.

Preferred G-quadruplex structures are those formed by the sequences d(TTAGGG)$_4$ (SEQ ID No. 1), d(AATGGGT)$_4$ (SEQ ID No. 5) and d(TTAGGGTT)$_4$ (SEQ ID No. 4). Several methods of determining the interaction of potential G-quadruplex interactive agents with these structures include UV/VIS spectroscopy, in which the changes in the UV/VIS spectrum of the potential agent under more than a 10% change at the wavelength due solely to the ligand and which undergoes the most change, upon addition of an excess of the G-quadruplex structure; UV spectroscopy, in which the melting temperature of the G-quadruplex structure as determined by a hyperchromicity transition at a given temperature range is increased by >50° C. upon addition of an excess of the agent; UV/VIS spectroscopy in which addition of a potential G-quadruplex interactive agent to a complex of a G-quadruplex-interactive perylene diimide and a G-quadruplex produces a >25% change in the absorption of due to the G-quadruplex-interactive perylene diimine-G-quadruplex complex; UV/VIS spectroscopy in which addition of a potential G-quadruplex interactive agent to a complex of a G-quadruplex-interactive carbocyanine and a G-quadruplex produces a >25% change in the absorption of due to the G-quadruplex-interactive carbocyanine-G-quadruplex complex; NMR spectroscopy in which the melting temperature of the G-quadruplex as determined by the disappearance of the imino proton signals of the G-quadruplex is increase by >5° C. in the presence of one- to two-equivalents of the agent; NMR spectroscopy in which the interaction of the agent with the G-quadruplex structure is determined by the shift of at least one of the imino protons of the G-quadruplex by >0.01 ppm upon addition of one- to two-equivalents of the agent; fluorescence spectroscopy in which the fluorescence emission spectrum of the agent undergoes a shift of >5 nm and/or a change in intensity of >25% upon the addition of an excess of the G-quadruplex structure; fluorescence spectroscopy in which the fluorescence emission spectrum of a G-quadruplex-interactive perylene diimide-G-quadruplex complex undergoes a >25% change upon the addition of an excess of the agent; or fluorescence spectroscopy in which the fluorescence emission spectrum of a G-quadruplex-interactive carbocyanine-G-quadruplex complex undergoes a >25% change upon the addition of an excess of the agent.

The preferred embodiments of the invention as it related to one class of G-quadruplex interactive telomerase inhibitors are compounds of the structure I in which

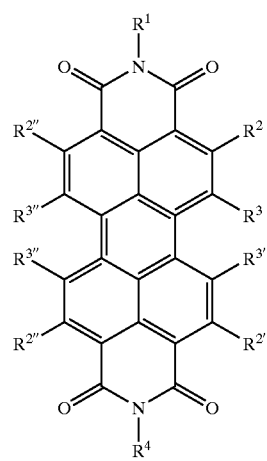

I in which $R^1$ and $R^4$ are independently taken from the set of sub-structures given by the formula -L-A in which L is a linking group taken from the set consisting of:

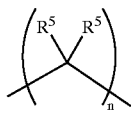

where n is 1, 2, or 3; and each R5 is independently taken from the set H, Me, OH, or OMe;

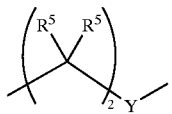

where R5 is as before and Y is taken from the set O, S, SO, SO2, NH, NMe, NCOMe;

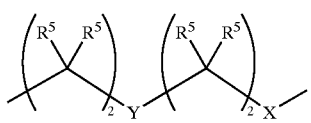

where R5 and Y are as before and X is taken from the set CH2, O, S, SO, SO2, NH, NMe, NCOMe;

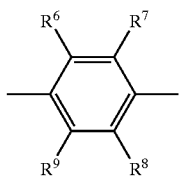

where R6, R7, R8, and R9 are independently taken from the set consisting of H, OMe, OEt, halo, or Me;
or a bond;
and A is taken from the set consisting of:

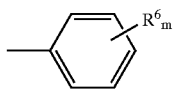

where m is 0–5 and each R6 is taken from the set consisting of halo, NH2, NO2, CN, OMe, SO2NH2, amidino, guanidino, or Me;

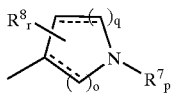

where o is 0 or 1; p is 0, 1, or 2; q is 1 or 2 such that o+q is either 2, in which case a pyrrolidine or pyrrole ring is indicated, or 3, in which a piperidine or pyridine ring is indicated; r is 0, 1, 2, or 3; R7 is H or Me; each R8 is independently taken from the set consisting of Me, NO2, OH, CH2OH, halo, or when r is 2 or 3, two adjacent R8 substituents may be together taken as —(CH=CH)2— or —(CH2)4— such as to form an annulated six-membered ring;

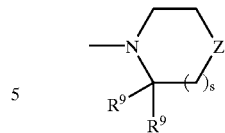

where each R9 is independently taken from the set consisting of H, Me, or both R9 can taken together be =O; s is equal to 0 or 1; and Z is taken from the set consisting of CH2, O, NH, NMe, NEt, N(Me)2, N(Et)2, or NCO2Et;

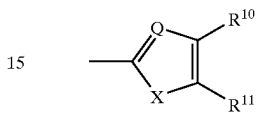

where Q is either N, CH, NMe, or NEt; X is either O, S, NH, NMe or NEt; R10 and R11 are independently taken from the set consisting of H, Me, CH2CO2Et, or R10 and R11 taken together consist of —(CH=CH)2— or —(CH2)4—;

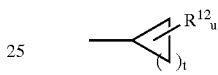

where t is equal to 1, 2, 3, or 4; u is equal to 0, 1, 2, 3, or 4, and each R12 is individually taken from the set consisting of Me, or OH;

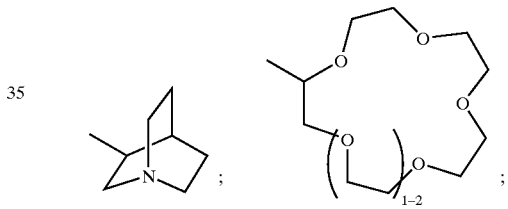

OH, $CO_2R^{13}$, $CON(R^{13})_2$, $SO_3H$, $SO_2N(R^{13})_2$, CN, $CH(CO_2R^{13})_2$, $CH(CON(R^{13})_2)_2$, $N(R^{13})_2$, or $N(R^{13})_3$ where R13 is either H, Me, Et, or $CH_2CH_2OH$;

R2, R2', R2", R2'''; R3, R3', R3", R3''' are each independently taken from the set H, OMe, halo, or NO2.

In addition, this invention includes the development of other G-quadruplex interactive telomerase inhibitors compounds derived from structure I, having the following structures:

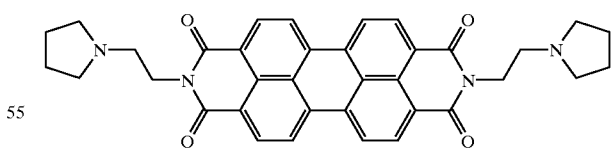

and

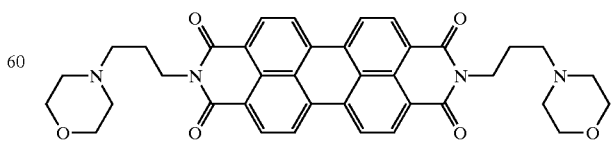

The preferred embodiment of the invention as it relates to another class of G-quadruplex interactive telomerase inhibitors are compounds of the general structure II:

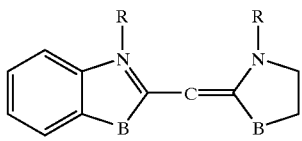

in which C is either a bond, —CH=CH—, —(CH=CH)2—, —(CH=CH)3—, p-phenylene, o-phenylene, p-phenylene-CH=CH—, or o-phenylene-CH=CH—; B is O, S, or NR, and R is either Me or Et.

In addition, this invention includes the development of another G-quadruplex interactive telomerase inhibitor compound derived from structure H, having the following structure:

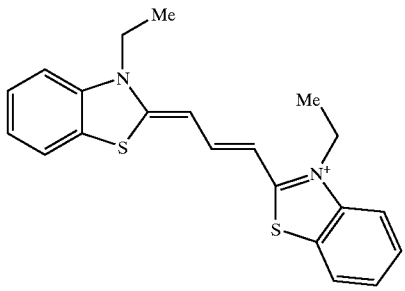

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF PREFERRED EMBODIMENTS

I. The Present Invention

Figure 1:
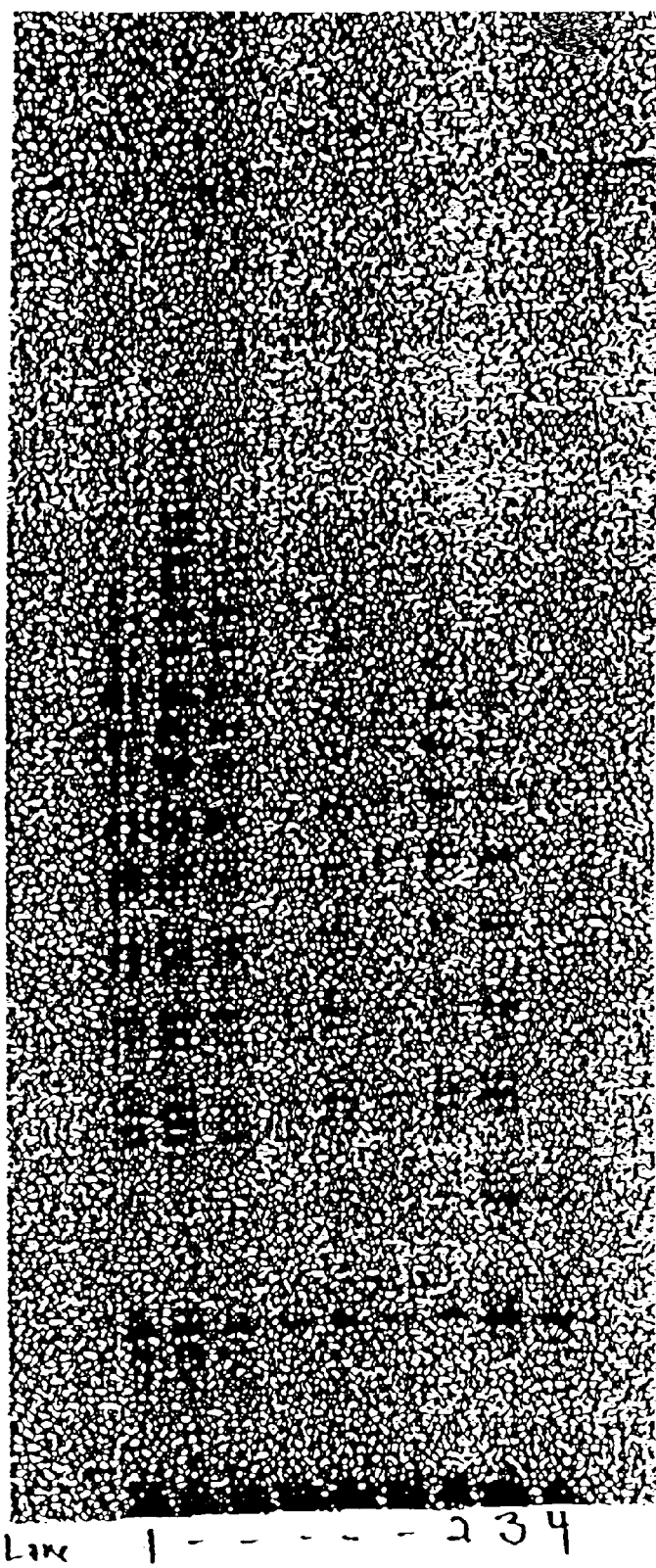
FIG. 1. Effect of increasing concentrations of N,N'-bis(2-dimethylaminoethyl)-3,4,9, 10-perylenetetracarboxylic acid diimide on inhibition of telomerase catalyzed extension of an 18-mer primer d[TTAGGG]$_3$ (SEQ ID No. 1) (1 $\mu$M). Elongated primer was labeled with 1.5 $\mu$M of [$\alpha$-$^{32}$P]-dGTP (800 Ci mmol$^{-1}$, 10 mCi ml$^{-1}$) with 1 mM dATP and dTTP using a standard telomerase assay. Lanes 1–5 are 0, 10, 50, and 100 $\mu$M of N,N'-bis(2-dimethylaminoethyl)-3,4,9,10-perylenetetracarboxylic acid diimide.
Figure 2:
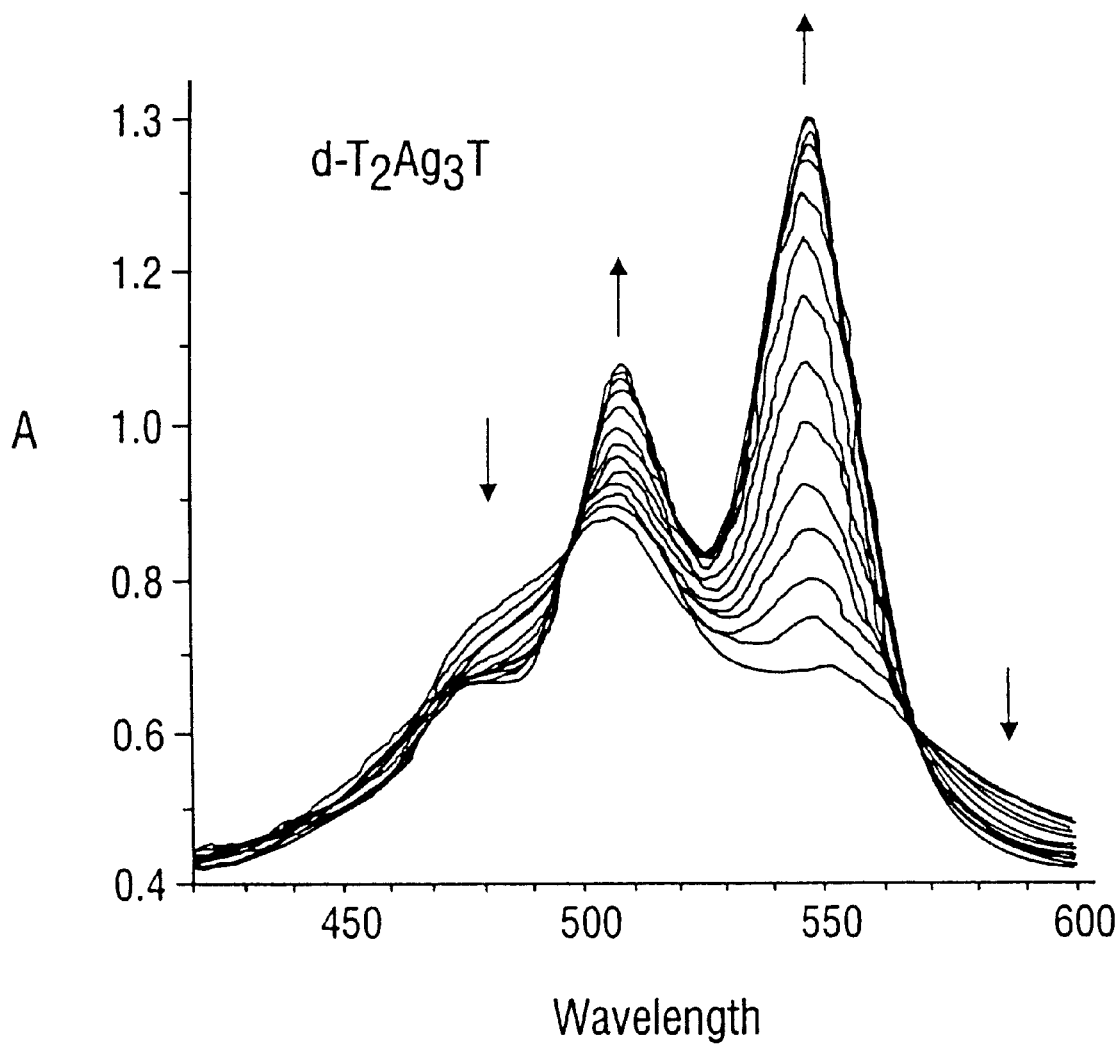
FIG. 2. Changes in the UV/VIS absorbance spectrum of N,N'-bis(2-dimethylaminoethyl)-3,4,9,10-perylenetetracarboxylic acid diimide upon addition of increasing amount of [d(TTAGGGT)]$_4$ (SEQ ID No. 6), an oligodeoxyribonucleotide which adopts a G-quadruplex structure.
Figure 3A:
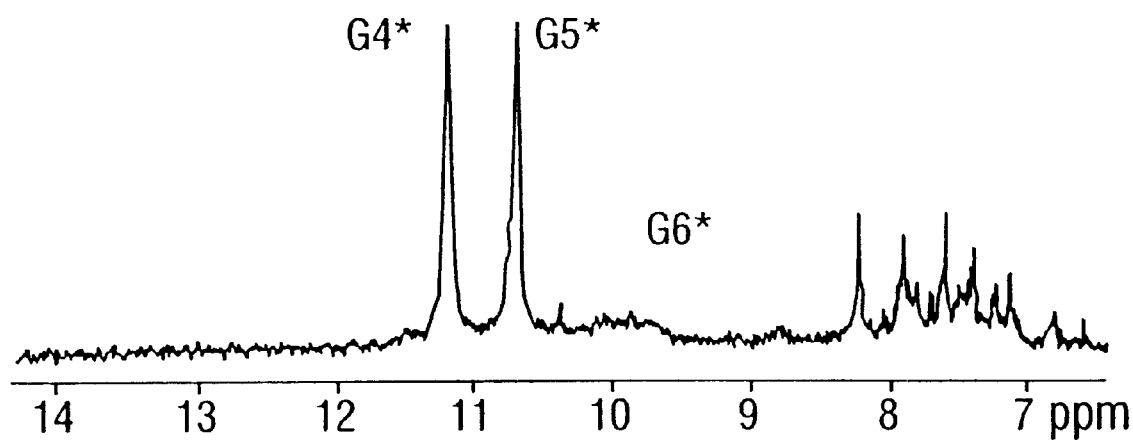
FIG. 3. Titration of [d(TTAGGGy]$_4$ (SEQ ID No. 1) with N,N'-bis(2-piperdinoethyl)-3,4,9,10-perylenetetracarboxylic acid diimide. Imino proton region of the 500-MHz 1H NMR is shown with increasing amounts of added ligand. The resonances labeled G4*, G5*, and G6* represent resonances of final 2:1 ligand/G-quadruplex complexes.
Figure 3B:
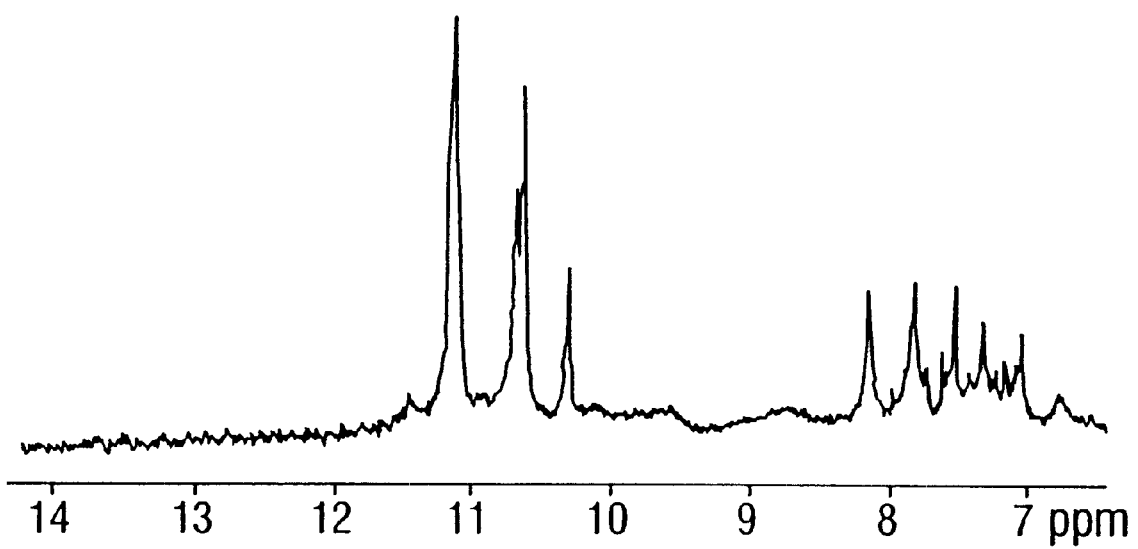
Figure 3C:
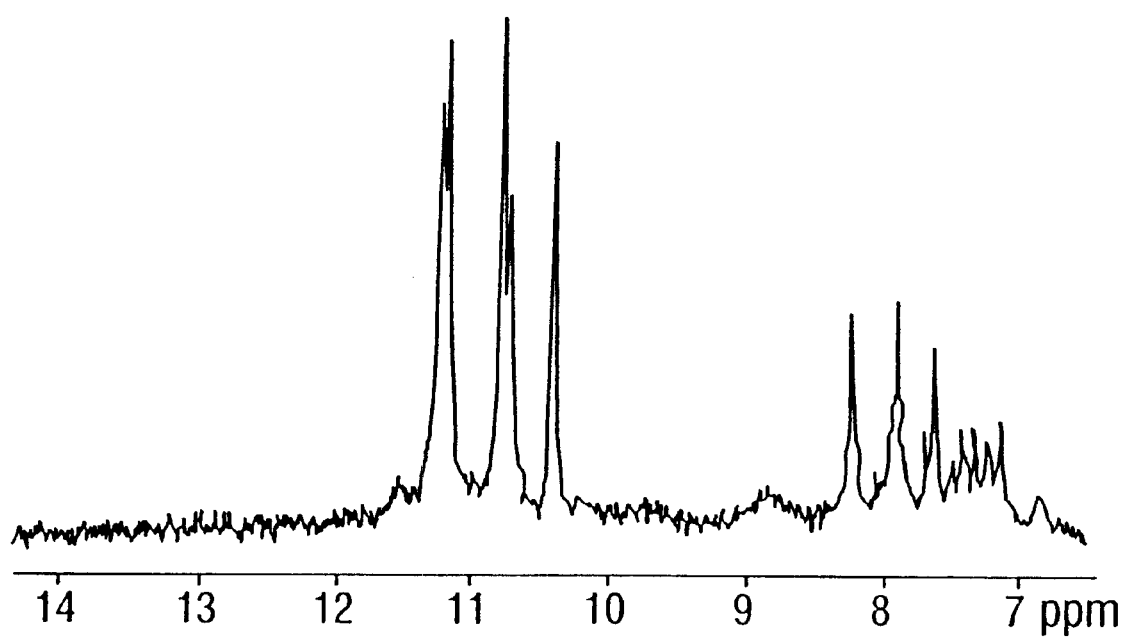
Figure 3D:
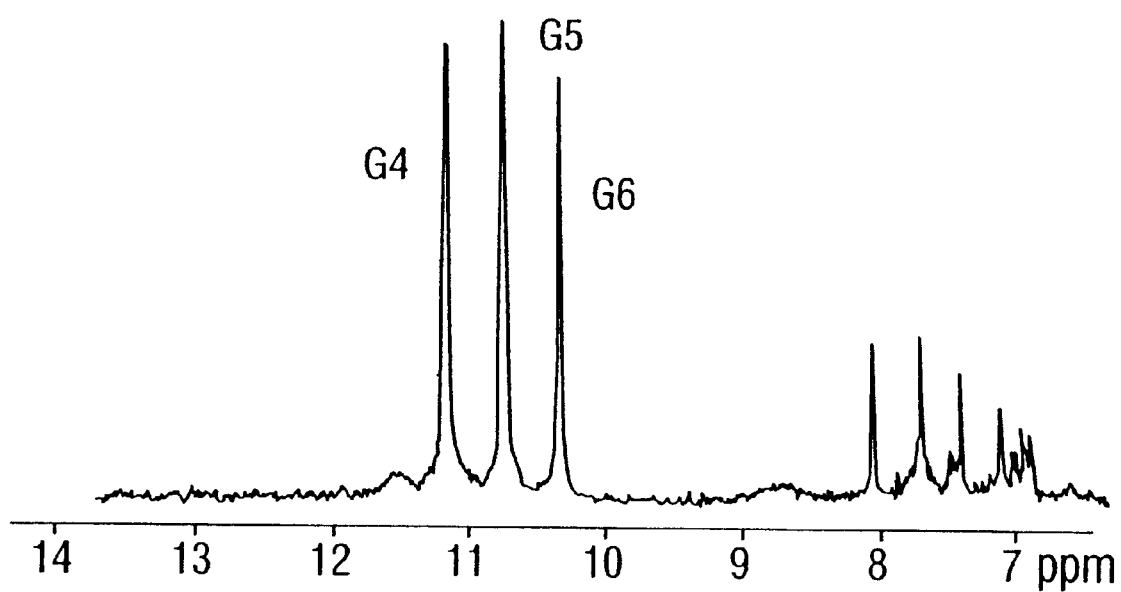
Figure 4:
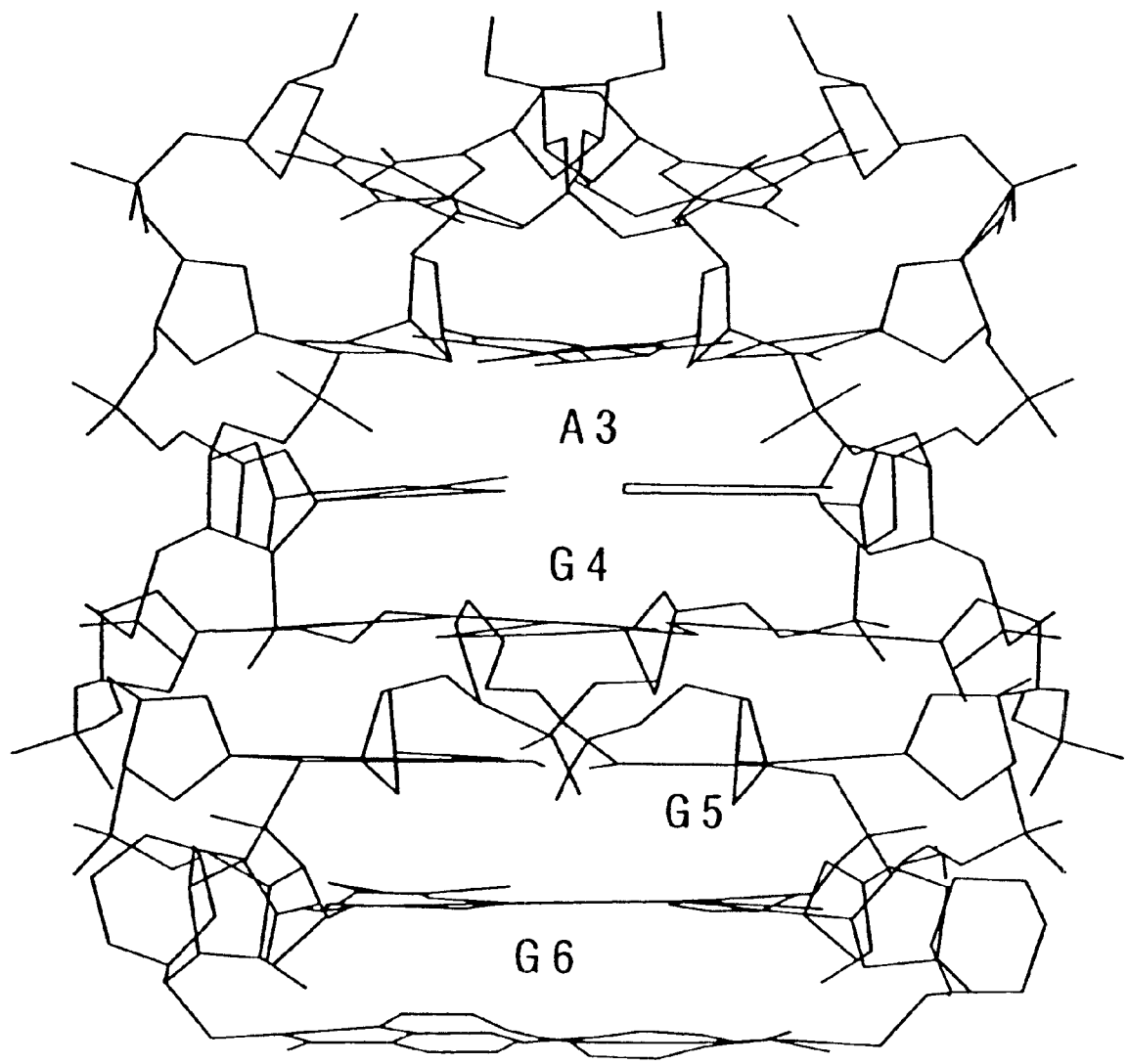
FIG. 4. NMR-based model of [d(TTAGGG)]$_4$ (SEQ ID No. 1)- N,N'-bis(2-piperdinoethyl)3,4,9,10-perylenetetracarboxylic acid diimide complex. The ligand is stacked under the G6 guanine tetrad with positively charged side chains located in the grooves.

A structure-based approach to discovering non-nucleoside compounds that will selectively inhibit human telomerase by targeting the nucleic acid structures, such as G-quadruplexes, that may be associated with human telomeres or telomerase has been utilized. Inhibition of human telomerase by a 2,6-diamido anthraquinone has been successfully demonstrated. $^1$H-NMR has demonstrated the stabilization of a G-quadruplex by this compound and evidence has been provided that this compound inhibits the telomerase enzyme by a mechanism consistent with interaction with G-quadruplex structures. The present work shows that non-nucleoside, small molecules can interact with G-quadruplexes and inhibit telomerase.

Using the methods described, it was found that compounds that bind to the human G-quadruplex structure inhibit the human telomerase. The identification of such G-quadruplex interactive agents is a novel and efficient approach for identifying human telomerase inhibitors.

It is envisioned that the telomerase inhibitors will provide therapy for tumors and cancers including skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood, lymphoid cancers and the like.

II. Telomerase

Telomerase is a ribonucleoprotein enzyme that synthesizes one strand of the telomeric DNA using as a template a sequence contained within the RNA component of the enzyme. The ends of chromosomes have specialized sequences, termed telomeres, comprising tandem repeats of simple DNA sequences which in humans is 5'-TTAGGG (SEQ ID No. 1) (Blackburn, 1991; Blackburn et al., 1995). Apart from protecting ends of chromosomes telomeres have several other functions, the most important of which appear to be associated with replication, regulating the cell cycle clock and ageing (Counter et al., 1992). Progressive rounds of cell division shorten telomeres by 50–200 nucleotides per round. Almost all tumor cells have shortened telomeres, which are maintained at a constant length (Allshire et al., 1988; Harley et al., 1990; Harley et al., 1994) and are associated with chromosome instability and cell immortalization.

With regard to human cells and tissues telomerase activity has been identified in immortal cell lines and in ovarian carcinoma but has not been detected at biologically significant levels (that are required to maintain telomere length over many cell divisions) in mortal cell strains or in normal non-germline tissues (Counter et al., 1992; Counter et al, 1994). These observations suggest telomerase activity is directly involved in telomere maintenance, linking this enzyme to cell immortality.

As described above, the immortalization of cells involves the activation of telomerase. More specifically, the connection between telomerase activity and the ability of many tumor cell lines, including skin, connective tissue, adipose, breast, lung, stomach, pancreas, ovary, cervix, uterus, kidney, bladder, colon, prostate, central nervous system (CNS), retina and blood tumor cell lines, to remain immortal has been demonstrated by analysis of telomerase activity (Kim, et al., 1994). This analysis, supplemented by data that indicates that the shortening of telomere length can provide the signal for replicative senescence in normal cells, see PCT Application No. 93/23572, incorporated herein by reference, demonstrates that inhibition of telomerase activity can be an effective anti-cancer therapy. Thus, telomerase activity can prevent the onset of otherwise normal replicative senescence by preventing the normal reduction of telomere length and the concurrent cessation of cell replication that occurs in normal somatic cells after many cell divisions. In cancer cells, where the malignant phenotype is due to loss of cell cycle or growth controls or other genetic damage, an absence of telomerase activity permits the loss of telomeric DNA during cell division, resulting in chromosomal rearrangements and aberrations that lead ultimately to cell death. However, in cancer cells having telomerase activity, telomeric DNA is not lost during cell division, thereby allowing the cancer cells to become immortal, leading to a terminal prognosis for the patient.

Methods for detecting telomerase activity, as well as for identifying compounds that regulate or affect telomerase activity, together with methods for therapy and diagnosis of cellular senescence and immortalization by controlling telomere length and telomerase activity, have also been described elsewhere.

A. G-Quadruplex Structures

Figure 5:
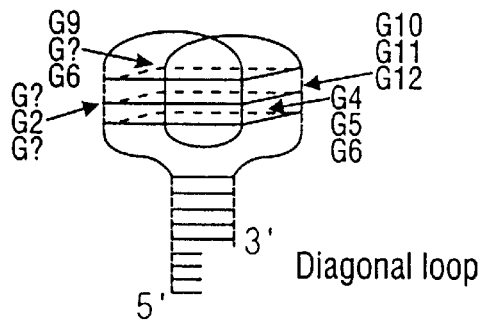
FIG. 5. Shows the design of an intramolecular quadruplex DNA that contains the human telomere repeats.

Human telomeres form structures known as G-quadruplexes. Human telomeres contain numerous repeats of the sequence TTAGGG (SEQ ID No. 1), exhibiting an enhancement of G and T residues and a paucity of A residues. Intramolecular G-quadruplex DNA may be designed by generating a sequence of human telomere repeats (FIG. 5). The G tetrad consists of four G bases hydrogen bonded in Hoogsteen fashion symmetrically disposed about a central axis, as shown in FIG. 5.

G-rich DNA is known to assume highly stable structures formed by Hoogsteen base pairs between guanine residues (Williamson, 1994; Nadel et at., 1995). These structures, known as G-quadruplexes, are stabilized in the presence of $K^-$ and may have biological roles that are yet to be determined (Henderson et at., 1987; Hardin et at., 1997; Williamson et at., 1989). One particular region of the genome where these structures may play a significant biological role is at the ends of chromosomes where G-rich DNA is normally found (e.g., TTAGGG (SEQ ID No. 1) and TTGGGG (SEQ ID No. 7) tandem repeats in human cells and ciliate Tetrahymena, respectively) (Henderson et at., 1987; Blackburn and Greider, 1995; Sundquist and Heaphy, 1993). In addition, a number of genes containing G-rich DNA have been identified recently, and it has been proposed that the G-rich regions within these genes may regulate gene expression by forming G-quadruplex structures (Sen and Gilbert, 1988; Hommond-Kosack et at., 1993; Murchie and Lilley, 1992; Simonsson et al., 1998). One potential biologically relevant role of G-quadruplex DNA is as a barrier to DNA synthesis (Howell et al., 1996). This barrier has been thoroughly investigated and has been found to be $K^+$dependent (Woodword et at., 1994). This observation strongly suggests that the formation of G-quadruplex species is responsible for the observed effect on DNA synthesis (Weitzmann et al., 1996).

The inventors have shown that the 2,6-diamidoanthraquinone BSU-1051 modulates human telomerase activity by a mechanism that is dependent on the elongation of the telomeric primer $d(TTAGGG)_3$ (SEQ ID No. 1) to a length that is then capable of forming an intramolecular G-quadruplex structure (Sun et al., 1997). The inventors have also shown that BSU-1051, by virtue of its interaction with G-quadruplex DNA, enhances the block of DNA synthesis by the G-quadruplex structure in the presence of $K^+$.

B. Methods for Identifying G-quadruplex Interactive Agents

Several methods for identifying classes of G-quadruplex interactive agents may be employed. One method involves identifying compounds whose three-dimensional structure is complementary to that of the G-quadruplex structure. G-quadruplex structure is understood to mean at least in one sense the structure of the G-quadruplex that is formed by the single-stranded DNA corresponding to at least four repeats of the telomeric sequence. In humans, the telomeric sequence is d(TTAGGG) (SEQ ID No. 1). Thus, the G-quadruplex structure of interest for the identification of human telomerase inhibitors may be any sequence of the form $\{d([N_1]TTAGGG[N_2])\}_4$ (SEQ ID No. 1) where $[N_1]$ is zero to two bases corresponding to the human telomeric sequence; for example, $[N_1]$ may equal G, GG, or may be absent; where $[N_2]$ is zero to three bases corresponding to the human telomeric sequence; for example, $[N_2]$ can equal T, TT, TTA or it may be absent.

Alternatively, G-quadruplex structure is understood to mean the fold-over or intramolecular G-quadruplex formed from at least four repeats of the G-triad of telomeric sequence. Thus, the G-quadruplex structure of interest for the identification of human telomerase inhibitors may be any sequence of the form $d([N_3][TTAGGG]_3[N_2])$ (SEQ ID No. 1 where $[N_2]$ is as defined above and $[N_3]$ is three G's preceded by zero to three nucleotides corresponding to the human telomeric sequence. These structures may be determined by a variety of techniques including molecular mechanics calculations, molecular dynamics calculations, constrained molecular dynamics calculations in which the constraints are determined by NMR spectroscopy, distance geometry in which the distance matrix is partially determined by NMR spectroscopy, x-ray diffraction, or neutron diffraction techniques. In the case of all these techniques, the structure can be determined in the presence or absence of any ligands known to interact with G-quadruplex structures, including but not limited to potassium and other metal ions, 2,6-diamidoanthraquinones, perylene diimides, or carbocyanines.

Complementary is understood to mean the existence of a chemical attraction between the G-quadruplex interactive agent and the G-quadruplex. The chemical interaction may be due to one or a variety of favorable interactions, including ionic, ion-dipole, dipole—dipole, van der Waals, charge-transfer, and hydrophobic interactions. Each of these type of interactions, alone or together, may be determined by existing computer programs using as inputs the structure of the compound, the structure of the G-quadruplex, and the relative orientation of the two. Such computer programs include but are not limited to AMBER, CHARMM, MM2, SYBYL, CHEMX, MACROMODEL, GRID, and BioSym. Such programs are contemplated as being useful for the determination of the chemical interaction between two molecules, either isolated, or surrounded by solvent molecules, such as water molecules, or using calculational techniques that approximate the effect of solvating the interacting molecules. The relative orientation of the two can be determined manually, by visual inspection, or by using other computer programs which generate a large number of possible orientations.

Examples of computer programs include but are not limited to DOCK and AutoDOCK. Each orientation can be tested for its degree of complementarity using the computer programs. An advantage of this method is that it does not require availability of physical samples of the compounds, only that their three-dimensional structure is known. It thus can be used to design novel compounds that possess the desired ability to inhibit telomerase.

Alternatively, this method may be used as a screening method for identifying telomerase inhibitors from a collection of compounds that are available, provided that the structure of these compounds is known. If only the two-dimensional structure is known, the corresponding three-dimensional structure can be obtained using existing computer programs. Such computer programs include but are not limited to CONCORD, CHEM3D, and MM2.

Another method for identifying G-quadruplex interactive compounds that may inhibit telomerase involves use of techniques such as UV/VIS spectroscopy, polarimetry, CD or ORD spectroscopy, IR or Raman spectroscopy, NMR spectroscopy, fluorescence spectroscopy, HPLC, gel electrophoresis, capillary gel electrophoresis, dialysis, refractometry, conductometry, atomic force microscopy, polarography, dielectometry, calorimetry, solubility, EPR or mass spectroscopy. The application of these methods can be direct, in which the G-quadruplex interactive compound's interaction with the G-quadruplex is measured directly, or it can be indirect, in which a particular G-quadruplex interactive agent having a useful spectroscopic property is used as a probe for the ability of other compounds to bind to the G-quadruplex; for example, by displacement or by fluorescence quenching.

III. Telomerase Inhibitors

The identification of compounds that inhibit telomerase activity provides important benefits to efforts at treating human disease. Compounds that inhibit telomerase activity can be used to treat cancer, as cancer cells express telomerase activity and normal human somatic cells do not express telomerase activity at biologically relevant levels (i.e. at levels sufficient to maintain telomere length over many cell divisions). Unfortunately, few such compounds have been identified and characterized. Hence, there remains a need for compounds that act as telomerase inhibitors and for compositions and methods for treating cancer and other diseases in telomerase activity is present abnormally. The present invention meets these and other needs.

Once a compound has been identified as being a G-quadruplex interactive agent, confirmatory evidence for the ability of said compound to inhibit telomerase may be obtained using a standard primer extension assay that does not use a PCR™-based amplification of the telomerase primer extension products such as described in Sun et al., 1997. The identified inhibitors may be used therapeutically to interfere with the function of telomerase and thus to treat cancers.

Using the screening methods described above, compounds have been identified that bind to human G-quadruplex structures and have been shown to inhibit human telomerase. One group of compounds is represented by general structure I:

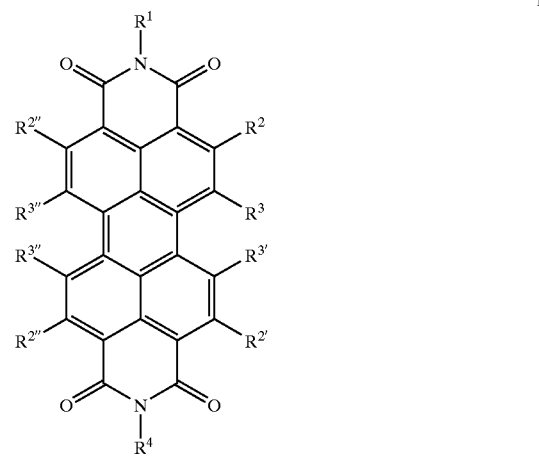

in which $R^1$ and $R^4$ are represented by L-A where L is a linking group which may be any of a group of substituted (X)methylene, (X)dimethylene, (X)trimethylene, (X)dimethyleneamine, (X)dimethyleneoxy, (X)dimethyleneaminodimethylene, (X)-dimethyleneoxydimethylene, (X)-p-phenylene, (X)-m-phenylene, (X)-o-phenylene, or an unsubstituted covalent bond;

A is a group that interacts with the grooves of the G-quadruplex structure, examples being a substituted carbocyclic ring, a (substituted) heterocyclic ring, an hydroxyl, a carboxylic acid, a carboxylic acid ester, a carboxamide, a sulfonamide, a sulfonic acid, a nitrile, a malonate diester, a malonate diamide, a disubstituted amine, a quarternized nitrogen-containing heterocyclce, or a quaternary amine.

R2, R2', R2'', R2''', R3, R3', R3'', R3''' are independently hydrogen, alkyl, halo, amino, nitro, hydroxy, alkoxy, alkylamino, dialkylamino, aryl, or cyano.

Another group of compounds suitable as telomerase inhibitors is shown by the general structure II in which B is O, S, or NR; C is an unsaturated linking group, 1 to 3 (substituted) ethylene groups, a substituted or unsubstituted carbocyclic group, or a heterocyclic group; and R is lower alkyl.

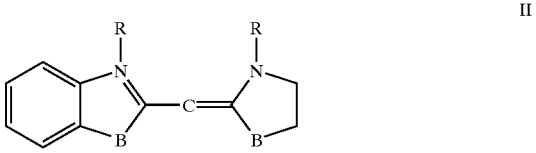

These compounds may interact specifically with G-quadruplex structures as compared to other nucleic acid structures such as double-stranded DNA, single-stranded DNA, and RNA structures. The degree of selectivity in the interaction of these compounds with G-quadruplex structures versus other nucleic acid structures is given by the ratio of the affinity of these compounds for G-qudruplex structures to the affinity for the other nucleic acid structures. In particular, the ability of these compounds to distinguish between G-quadruplex structures and double-stranded DNA may be an important criterion. Compounds with general ability to bind double-stranded DNA are known to inhibit or alter a variety of DNA-associated enzymes or proteins, including but not limited to: histone binding, topoisomerase I, topoisomerase II, DNA-polymerases, RNA-polymerases, DNA repair enzymes, cytosine methyltransferase, and transcription factor binding. In order to discover compounds that are able to selectively inhibit telomerase and other G-qudruplex-associated enzymes and proteins, one would want to select compounds that have a high ratio of affinities for G-qudruplex structures versus double-stranded DNA. These selective G-quadruplex-binding compounds can be identified by selecting those G-quadruplex binding compounds that display weak or no ability for binding to double-stranded DNA, as determined by UV/VIS spectroscopy, polarimetry, CD or ORD spectroscopy, IR or Raman spectroscopy, NMR spectroscopy, fluorescence spectroscopy, HPLC, gel electrophoresis, capillary gel electrophoresis, dialysis, refractometry, conductometry, atomic force microscopy, polarography, dielectometry, calorimetry, solubility, EPR and mass spectroscopy.

In addition to the thermodynamic considerations of G-quadruplex binding by these compounds, the kinetics of the interaction between these compounds and G-quadruplexes is also considered to be important. The relative rates of the association and dissociation of these compounds with G-quadruplex structures can affect their biological properties. In particular, those compounds with slow dissociation rates may be more effective in inhibiting telomerase and other G-quadruplex-associated enzymes and proteins than hose with identical G-quadruplex binding ability, but whose dissociation rates are faster. For a given compound, the overall equilibrium binding affinity (binding constant) to G-quadruplex structures is a ratio of the association rate and the dissociation rate. The dissociation rate of a complex consisting of a G-quadruplex structure and a G-quadruplex interactive compound can be determined by a variety of methods. In one example, the dissociation of the complex can be determined spectrophotometrically upon the addition of a detergent, such as SDS. Alternatively, the dissociation rate can be determined in a T-jump study, in which the temperature of the complex is quickly raised to a point at which the complex dissociates and this process is monitored spectrophotometrically. In another example the dissociation rate for a G-quadruplex-compound complex can be determined by monitoring by a variety of techniques the dissociation of a complex in which one partner, either the G-quadruplex or the compound, is tethered, either covalently or non-covalently, to an immobile phase, and a solution is passed over this immobilized complex. The dissociation rate for a G-quadruplex-compound complex also can be determined indirectly, by measuring both the equilibrium binding constant and the association rate. For example, if two compounds have similar equilibrium G-quadruplex binding constants, but one has a slower association rate, then that same compound must also have a proportionately slow dissociation rate.

Using the above techniques, one can select from those G-quadruplex interactive agents identified, those that have additional desired properties of selective G-quadruplex interaction when compared to other nucleic acids structures, such as double-stranded DNA, and/or slow kinetics of association with G-quadruplex structures.

Agents capable of inhibiting telomerase activity in tumor cells offer therapeutic benefits with respect to a wide variety of cancers and other conditions (for example, fungal infections) in which immortalized cells telomerase activity are a factor in disease progression or in which inhibition of telomerase activity is desired for treatment purposes. The telomerase inhibitors of the invention can also be used to inhibit telomerase activity in germ line cells, which may be useful for contraceptive purposes.

IV. Pharmaceutical Formulations and Administration

The invention further comprises the therapeutic treatment of cancer by the administration of an effective dose of one or more inhibitors of telomerase. Where clinical applications are contemplated, it will be necessary to prepare pharmaceutical compositions of drugs in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. A preferred route is direct intra-tumoral injection, injection into the tumor vasculature or local or regional administration relative to the tumor site.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compounds developed in the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Because telomerase is active only in tumor, germline, and certain stem cells of the hematopoietic system, other normal cells are not affected by telomerase inhibition therapy Steps also can be taken to avoid contact of telomerase inhibitor with germline or stem cells, although this may not be essential. For instance, because germline cells express telomerase activity, inhibition telomerase may negatively impact spermatogenesis and sperm viability, suggesting that telomerase inhibitors may be effective contraceptives or sterilization agents. This contraceptive effect may not be desired, however, by a patient receiving a telomerase inhibitor of the invention for treatment of cancer. In such cases, one can deliver a telomerase inhibitor of the invention in a manner that ensures the inhibitor will only be produced during the period of therapy, such that the negative impact on germline cells is only transient.

V. Therapies

One of the major challenges in oncology today is the effective treatment of a given tumor. Tumors are often resistant to traditional therapies. Thus, a great deal of effort is being directed at finding efficous treatment of cancer. One way of achieving this is by combining new drugs with the traditional therapies and is discussed below. In the context of the present invention, it is contemplated that therapies directed against telomerase could be used in conjunction with surgery, chemotherapy, radiotherapy and indeed gene therapeutic intervention. It also may prove effective to combine telomerase targeted chemotherapy with antisense or immunotherapies directed toward tumor markers or other oncogenes or oncoproteins.

"Effective amounts" are those amounts of a candidate substance effective to reproducibly decrease expression of telomerase in an assay in comparison to levels in untreated cells. An "effective amount" also is defined as an amount that will decrease, reduce, inhibit or otherwise abrogate the growth of a cancer cell.

It is envisioned that the telomerase inhibitors will provide therapy for a wide variety of tumors and cancers including skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood and lymphoid cancers.

A. Combination Therapies

To kill cells, inhibit cell growth, inhibit metastasis, inhibit angiogenesis or otherwise reverse or reduce the malignant phenotype of tumor cells, the methods of standard therapy discussed above are generally insufficient as tumors are often resistant to several of these agents. Often combining a host of different treatment methods prove most effective in cancer therapy. Further, several AIDS afflicted patients have a higher risk of developing cancers. Combination therapy in these cases is required to treat AIDS as well as the cancer. Using the methods and compounds developed in the present invention, one would generally contact a "target" cell with a telomerase inhibitor and at least one other agent. These compositions would be provided in a combined amount effective to kill or inhibit proliferation of the cell. This process may involve contacting the cells with the telomerase based therapy and the other agent(s) or factor(s) at the same time. This may also be achieved by contacting the cell with a single composition or pharmacological formulation that includes both agents, or by contacting the cell with two distinct compositions or formulations, at the same time, wherein one composition includes the telomerase based therapy and the other includes the agent.

Alternatively, the telomerase inhibitor-based treatment may precede or follow the other agent treatment by intervals ranging from min to wk. In embodiments where the other agent and telomerase-based therapy are applied separately to the cell, one would generally ensure that a significant period of time did not expire between the time of each delivery, such that the agent and telomerase-based treatment would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several days (2, 3, 4, 5, 6 or 7) to several wk (1, 2, 3, 4, 5, 6, 7 or 8) lapse between the respective administrations.

It also is conceivable that more than one administration of either telomerase-based treatment or the other agent will be desired. Various combinations may be employed, where telomerase-based treatment is "A" and the other agent is "B", as exemplified below:

A/B/A B/A/B B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/B/A/A A/A/B/A

A/B/B/B B/A/B/B B/B/A/B

Other combinations are also contemplated. Again, to achieve cell killing, both agents are delivered to a cell in a combined amount effective to kill the cell.

The invention also encompasses the use of a combination of one or more DNA damaging agents, whether chemotherapeutic compounds or radiotherapeutics as described in the section below, together with the telomerase inhibitor. The invention also contemplates the use of the telomerase inhibitors in combination with surgical removal of tumors to treat any remaining neoplastic or metastasized cells. Further, immunotherapy may be directed at tumor antigen markers that are found on the surface of tumor cells. The invention also contemplates the use of telomerase inhibitors in combination with gene therapy, directed toward a variety of oncogenes, such as, tumor markers, cell cycle controlling genes, described below.

The other agent may be prepared and used as a combined therapeutic composition, or kit, by combining it with the telomerase-inhibitor based treatment, as described above. The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It is proposed that the regional delivery of non-nucleoside inhibitors of telomerase to patients with tumors will be a very efficient method for delivering a therapeutically effective chemical to counteract the clinical disease. Similarly, other chemotherapeutics, radiotherapeutics, gene therapeutic agents may be directed to a particular, affected region of the subjects body. Alternatively, systemic delivery of telomerase based treatment and/or the agent may be appropriate in certain circumstances, for example, where extensive metastasis has occurred.

It also should be pointed out that any of the standard or other therapies may prove useful by themselves in treating a cancer. In this regard, reference to chemotherapeutics and non-telomerase inhibitor-based treatment in combination should also be read as a contemplation that these approaches may be employed separately.

When such combination therapy is employed for the treatment of a tumor, the cytotoxic agent may be administered at a dosage known in the art to be effective for treating the tumor. However, the G-quadruplex interaction compounds may produce an additive or synergistic effect with a cytotoxic agent against a particular tumor. Thus, when such combination antitumor therapy is used, the dosage of G-quadruplex interaction compounds administered may be less than that administered when the cytotoxic agent is used alone. Similarly, for patients afflicted by AIDS, AZT/protease inhibitors will be used with G-quadruplex interaction compounds, or other herein mentioned therapeutic agent(s). Again the dosage of G-quadruplex interaction compounds or other conjunctively utilized agent, may be altered to suit the AIDS treatment.

Preferably, the patient is treated with G-quadruplex interaction compounds for about 1 to 14 days, preferably 4 to 14 days, prior to the beginning of therapy with a cytotoxic agent, and thereafter, on a daily basis during the course of such therapy. Daily treatment with the telomerase inhibitor can be continued for a period of, for example, 1 to 365 days after the last dose of the cytotoxic agent is administered. This invention encompasses the use of telomerase inhibitors-based cancer therapy for a wide variety of tumors and cancers affecting skin, connective tissues, adipose, breast, lung, stomach, pancreas, ovary, cervix, uterus, kidney, bladder, colon, prostate, anogenital, central nervous system (CNS), retina and blood and lymph.

B. Standard Therapies

Described herein are the therapies used as standard or traditional methods for treatment of cancers. The section on chemotherapy describes the use of non-nucleoside telomerase inhibitors as chemotherapeutic agents in addition to several other well known chemotherapeutic agents. As detailed in the section above, all the methods described below can be used in combination with the telomerase inhibitors developed in the present invention.

a. Surgery: Surgical treatment for removal of the cancerous growth is generally a standard procedure for the treatment of tumors and cancers. This attempts to remove the entire cancerous growth. However, surgery is generally combined with chemotherapy and/or radiotherapy to ensure the destruction of any remaining neoplastic or malignant cells.

b. Chemotherapy: A variety of chemical compounds, also described as "chemotherapeutic agents", function to induce DNA damage, are used to treat tumors. Chemotherapeutic agents contemplated to be of use, include, adriamycin, 5-fluorouracil (5FU), etoposide (VP-16), camptothecin, actinomycin-D, mitomycin, cisplatin (CDDP), hydrogen peroxide, carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, tamoxifen, taxol, transplatinum, vincristin, vinblastin and methotrexate to mention a few.

Agents that damage DNA include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. A number of such agents have been developed, particularly useful are agents that have undergone extensive testing and are readily available. 5-fluorouracil (5-FU), is one such agent that is preferentially used by neoplastic tissue, making it particularly useful for targeting neoplastic cells. Thus, although quite toxic, 5-FU, is applicable with a wide range of carriers, including topical and even intravenous administrations with doses ranging from 3 to 15 mg/kg/day.

Agents that directly cross-link nucleic acids, specifically DNA, are envisaged to facilitate DNA damage leading to a useful antineoplastic treatment. For example, cisplatin, and other DNA alkylating agents may be used. Cisplatin has been widely used to treat cancer, with efficacious doses used in clinical applications of 20 mg/m$^2$ for 5 days every three wk for a total of three courses. Cisplatin is not absorbed orally and must therefore be delivered via injection intravenously, subcutaneously, intratumorally or intraperitoneally.

Figure 7:
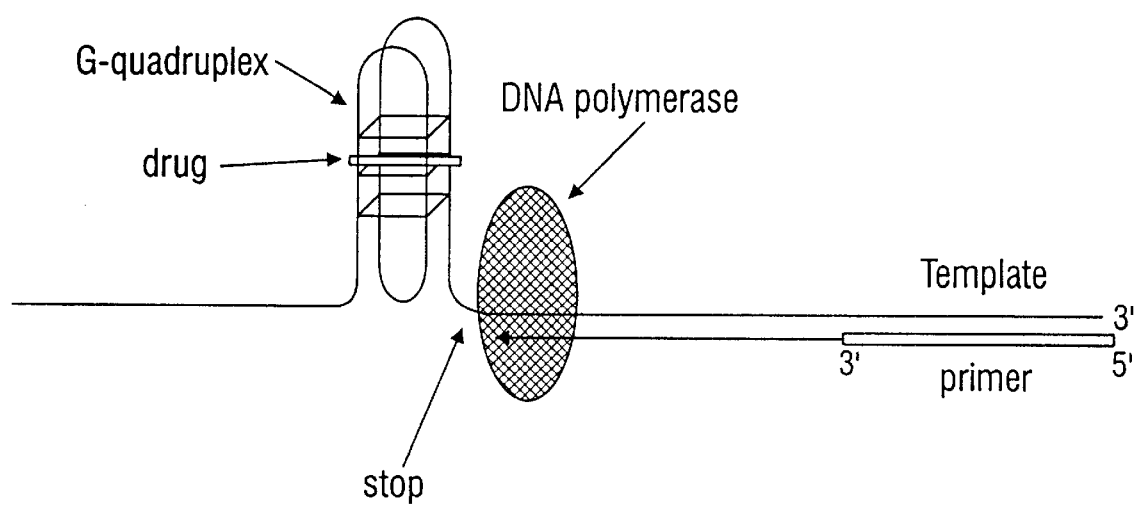
FIG. 7. Model depicting G-quadruplex structure blocking primer extension by DNA polymerase.

The non-nucleoside G-quadruplex inhibitor compounds developed in this invention are chemotherapeutic agents that are cytotoxic and inhibit telomerase function which is critical to cell replication and maintenance of tumor cell immortality. These compounds also indirectly inhibit DNA polymerases by their strong interactions with the G-quadruplex structures (FIG. 7).

c. Radiotherapy: Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiation's. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

d. Gene Therapy: Gene therapy based treatments targeted towards oncogenes such as p53, p16, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl, which are often mutated versions of their normal cellular counterparts in cancerous tissues.

VI. Screening for Anti-telomere and Anti-cancer Activity

In particular embodiments, one may test the inhibitors by measuring their ability to inhibit growth of cancer cells, to induce cytotoxic events in cancer cells, to induce apoptosis of the cancer cells, to reduce tumor burden and to inhibit metastases. For example, one can measure cell growth according to the MTT assay. A significant inhibition in growth is represented by decreases of at least about 30%–40% as compared to uninhibited, and most preferably, of at least about 50%, with more significant decreases also being possible. Growth assays as measured by the MTT assay are well known in the art. Other assays to measure cell death, apoptosis are well known in the art, for example, Mosmann et al., 1983; Rubinstein et al., 1990.

Quantitative in vitro testing of the anti-tumor agents identified herein is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Telomerase Inhibition by N,N'-bis(2-dimethylaminoethyl)-3,4,9,10-perylenetetracarboxylic acid diimide Selection of N,N'-bis(2-dimethylaminoethyl)-3,4,9,10-perylenetetracarboxylic acid diimide as a potential telomerase inhibitor was determined by Method (B) as described in Example 2.

1

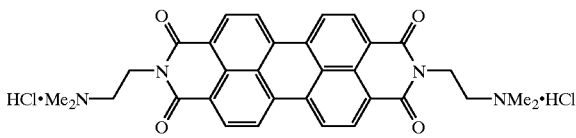

The relative inhibition of telomerase by N,N'-bis(2-dimethylaminoethyl)3,4,9,10-perylenetetracarboxylic acid diimide was determined in a standard primer extension assay that does not use a PCR™-based amplification of the telomerase primer extension products. Briefly, the 18-mer telomeric primer d[TTAGGG]$_3$ (SEQ ID No. 1) (1 μM) without or with N,N'-bis(2-dimethylaminoethyl)-3,4,9,10-perylenetetracarboxylic acid diimide was elongated with telomerase in the presence of 1.5 μM of [α-$^{32}$P]-dGTP (800 Ci mmol$^{-1}$, 10 mCi ml$^{-1}$) with 1 mM dATP and 1 mM dTTP. The extension products were isolated and visualized by autoradiography after denaturing gel electrophoresis.

The IC$_{50}$ was determined to be 50 μM, and at 100 μM of N,N'-bis(2-dimethylaminoethyl)3,4,9,10-perylenetetracarboxylic acid diimide there is an almost complete inhibition of telomerase activity. N,N'-bis(2-piperdinoethyl)-3,4,9,10-perylenetetracarboxylic acid diimide and 3 showed similar behavior.

2

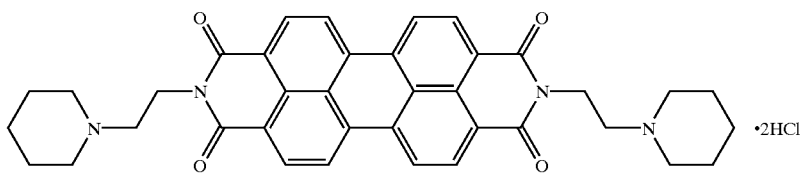

Example 2

Screening Assays for Telomerase Inhibitors

Compounds that inhibit telomerase are potential drugs for the treatment of cancer. The method selects compounds based upon ability to interact with the human DNA-G-quadruplex. Several procedures for detecting this interaction include:

(A) A three dimensional structure of a candidate compound will be analyzed to determine their degree of complementarity to the three-dimensional structure of human telomeric DNA G-quadruplex. The NMR solution structure of d(AGGGTTAGGGTTAGGGTTAGGG) (SEQ ID No. 8) [pdb entry 143d] and its corresponding molecular surface, generated with the ms program, were used as inputs to the SPHGEN program. The resulting sphere cluster was used as input to DOCKv2.0 and a subset of the Cambridge crystallographic database was search using the contact scoring algorithm. N,N'-bis(2-dimethylaminoethyl)-3,4,9,10-perylenetetracarboxylic acid diimide was found to have one of the highest contact scores in the ~2000 compounds examined.

(B) Compounds may be selected for their ability to interact with human DNA G-quadruplex as indicated by UV/VIS spectroscopy. To a 10 μM solution of N,N'-bis(2-dimethylaminoethyl)-3,4,9,10-perylenetetracarboxylic acid diimide in 20 mM phosphate buffer containing 100 mM KCl, pH 7.0 in a quartz cuvette was added 10 μL aliquots of a 3 mM solution of d(TTAGGGT)$_4$ (SEQ ID No. 6). After each addition the UV/VIS spectrum was recorded. Pronounced changes in the UV/VIS spectrum of the compound were noted at wavelengths 488 nm (~40% hypochromicity), 510 nm 50% hyperchromicity), and 548 nm (~200% hyperchromicity).

(C) Compounds may be selected for their ability to interact with human DNA G-quadruplex as indicated by NMR spectroscopy. The imino proton spectrum (9–12 ppm) of a solution of d(TTAGGG)4 (SEQ ID No. 1) in D2O/H2O (10:90) was determined at 500 MHz. Aliquot of N,N'-bis(2-piperdinoethyl)-3,4,9,10-perylenetetracarboxylic acid diimide were added and the imino proton spectrum recorded. At an overall stoichiometry of 1:1 the G6 imino resonance becomes significantly broader and shifts >0.2 ppm upfield.

(D) Compounds may be selected for their ability to interact with human DNA g-quadruplex as indicated by an increase in the melting temperature of the G-quadruplex structure. Thermal denaturation of the parallel four-stranded G-quadruplex structure formed by the d[T$_2$AG$_3$T] (7-mer) (125 mM KCl, 25 mM KH$_2$PO$_4$, 1 mM EDTA, pH 6.9) monitored by NMR. The spectrum for DNA alone and in the presence of N,N'-bis(2-dimethylaminoethyl)-3,4,9,10-perylenetetracarboxylic acid diimide. The molar ratio of N,N'-bis(2-dimethylaminoethyl)-3,4,9,10-perylenetetracarboxylic acid diimide to quadruplex was 4:1. The imino proton signals have been assigned previously (Laughlan et al., 1994) as G6, G5, and G4 from high to low field. The presence of drug leads to line broadening and an upfield shift of the imino proton signals indicative of intercalation. Furthermore, the melting temperature of the DNA G-quadruplex is increased significantly in the presence of the compound. Spectra were acquired in 90% H$_2$O/10% D$_2$O on a Bruker AMX 500 MHz spectrometer at various 15–85° C. using a 1—1 echo pulse sequence with a maximum excitation centered at 12.0 ppm. A total of 128 scans was obtained for each spectrum with a relaxation delay of 2 s. Before acquiring the spectrum at each temperature, the sample was allowed to equilibrate at the new temperature for at least 10 min. The data were processed with an exponential window function using 2 Hz of line broadening. The data indicate that N,N'-bis(2-dimethylaminoethyl)-3,4,9,10-perylenetetracarboxylic acid diimide increases the melting temperature of the G-quadruplex by at least 20° C.

Example 3

Synthesis of N,N'-bis(2-piperdinoethyl)-3,4,9,10-perylenetetracarboxylic acid diimide N,N'-bis(2-piperdinoethyl)-3,4,9,10-perylenetetracarboxylic acid diimide was prepared by mixing three g of 3,4,9,10-perylenetetracarboxylic acid dianhydride with 2.5 mL of 1-(2-aminoethyl)piperidine in 10 mL of DMA and 10 mL of 1,4-dioxane. The mixture was heated under reflux for 6 hours, and the solvents removed under reduced pressure. The residue was dissolved in ~100 mL of distilled water, and insoluble components were removed by filtration. The pH of the resulting solution was adjusted to ~3 with the addition of HCl, and the solution was allowed to stand overnight. Precipitated impurities was removed by filtration, and the resulting solution was adjusted to pH 1–12 with the addition of NaOH. The precipitated product was isolated by filtration, washed with water and dried under vacuum.

Example 4

DNA Synthesis Arrest Assay

It has been shown that DNA sequences with quadruplex-forming potential present obstacles to DNA synthesis by DNA polymerases in a $K^+$ dependent manner. This $K^+$ dependent block to DNA polymerase is a selective and sensitive indicator of the formation of intramolecular quadruplexes (Weitzmann, et al., 1996). This assay has been adapted to demonstrate the stabilization of quadruplex by small molecules and used to screen potential G-quadruplex-interactive compounds.

The assay is a modification of that described by Weitzmann, et al. Briefly, primers (24 nM, sequence: 5'-TAATACGACTCACTATAG-3') (SEQ ID No. 9) labeled with [γ-$^{32}$P]ATP were mixed with template DNA PQ74(12 nM, (SEQ ID No. 10)
sequence: TCCAACTATGTATACTTGGGGTTGGGGTTGGGG

TTGGGGTTGGGGTTAGCGGCACGCAATTGCTATAGTGAGTCGTATTA-

ID No. 10) in a Tris-HCl buffer (10 mM Tris, pH 8.0) containing 5 mM $K^+$and heated at 90° C. for 4 min. After cooling at room temperature for 15 min. potential G-quadruplex-interactive compounds were then added to various concentrations. The primer extension reactions were initiated by adding dNTP (final concentration 100 μM), $MgCl_2$ (final concentration 3 mM) and Taq polymerase (2.5 U/reaction, Boehringer Mannheim). The reactions were incubated at 55° C. for 15 mm. then stopped by adding an equal volume of stop buffer (95% formamide, 10 mM EDTA, 10 mM NaOH, 0.1% xylene cyanol, 0.1% bromophenol blue). The products were separated on a 12% polyacrylamide sequencing gel. The gels were then dried and visualized on a phosphorimager (Molecular Dynamics model 445 S1).

Figure 8:
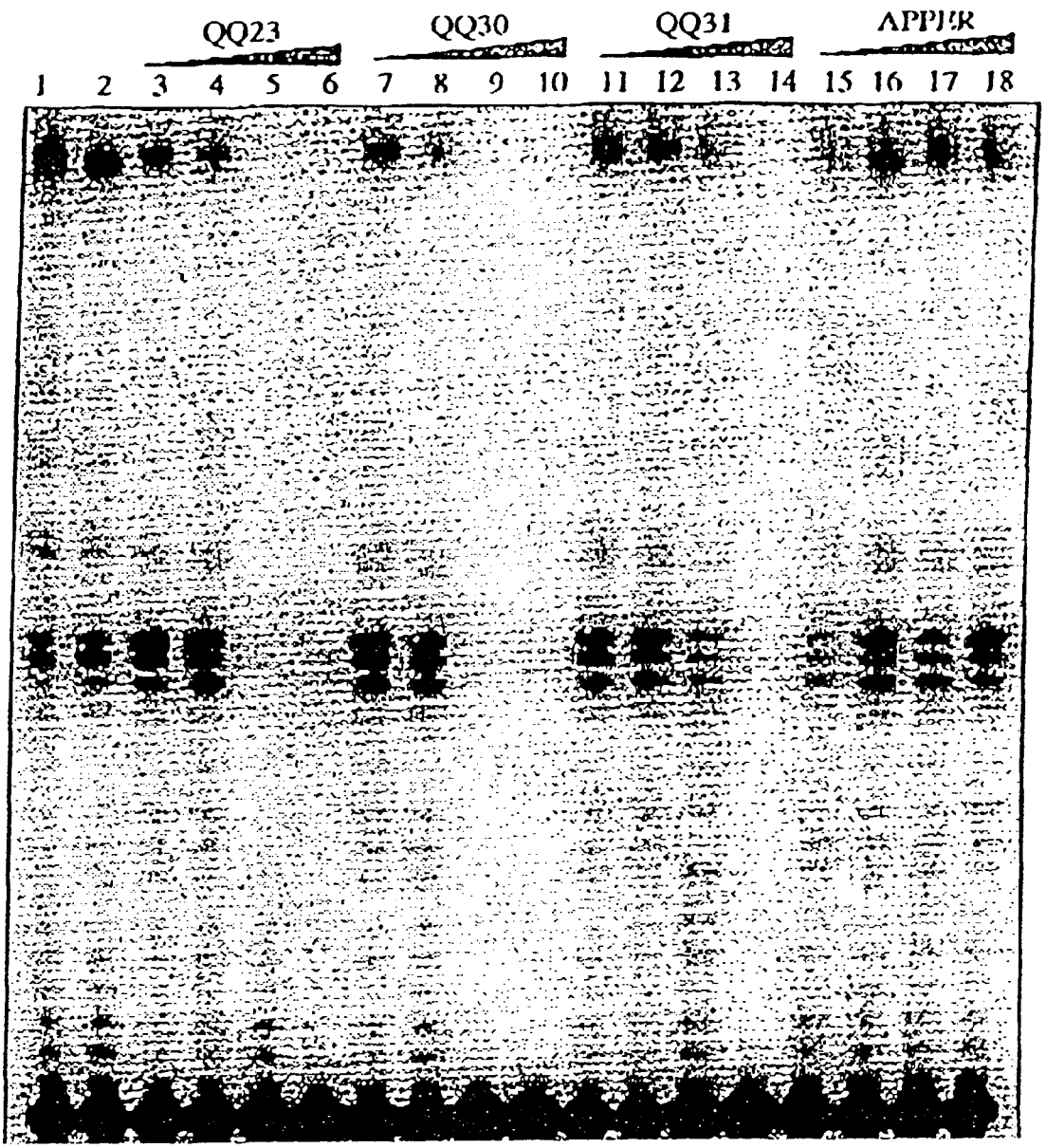
FIG. 8. Primer extension of PQ sequence in the presence of compounds. Lane 1: water control; Lane 2: 50 mM K+; Lanes 3–6; QQ23; Lanes 7–10; QQ30; Lanes 11–14; QQ31; Lanes 15–18; APPER (Bis[1-(2-aminoethyl)piperdine]-3, 4, 9, 10-perylenetetracarboxylic diimide); Lanes 3, 7, 11, and 15; 0.5 $\mu$M; Lanes 4, 6, 12,and 16; 1 $\mu$M; Lanes 5, 9, 13 and 17; 10 $\mu$M; Lanes 6, 10, 14 and 18; 50 $\mu$M.

To validate the assay, G-quadruplex interactive compounds such as porphyrins and perylenes were tested. The results were consistent with NMR and telomerase inhibition data. FIG. 8 shows the DNA synthesis arrest induced by Quinobenzoxazine analogs (QQ23, 1130, QQ31) and a perylene compound (APPER).

Example 5

Photocleavage Assay to Detect Quadruplex DNA Interactions (i) Design and Synthesis of an Intramolecular Quadruplex DNA The oligonucleotide G4A employed was synthesized on a Perseptive DNA synthesizer and deprotected following the routine phosporamidite procedures. the DNA was purified by polyacrylamide gel electrophoresis (PAGE). The sequence for this 39 oligomer single strand DNA is:
5' CATGGTGGTTTGGGTTAGGGTTAGGGT-TAGGGTTACCAC 3' (SEQ ID No. 11).

This human telomere repeat-containing DNA was designed to form an intramolecular quadruplex which can be stabilized by the stem region in (FIG. 5). A sticky end was added so that unusual secondary structures could be detected by ligation assay once they are formed.

(ii) Photocleavage Assay

Figure 6:
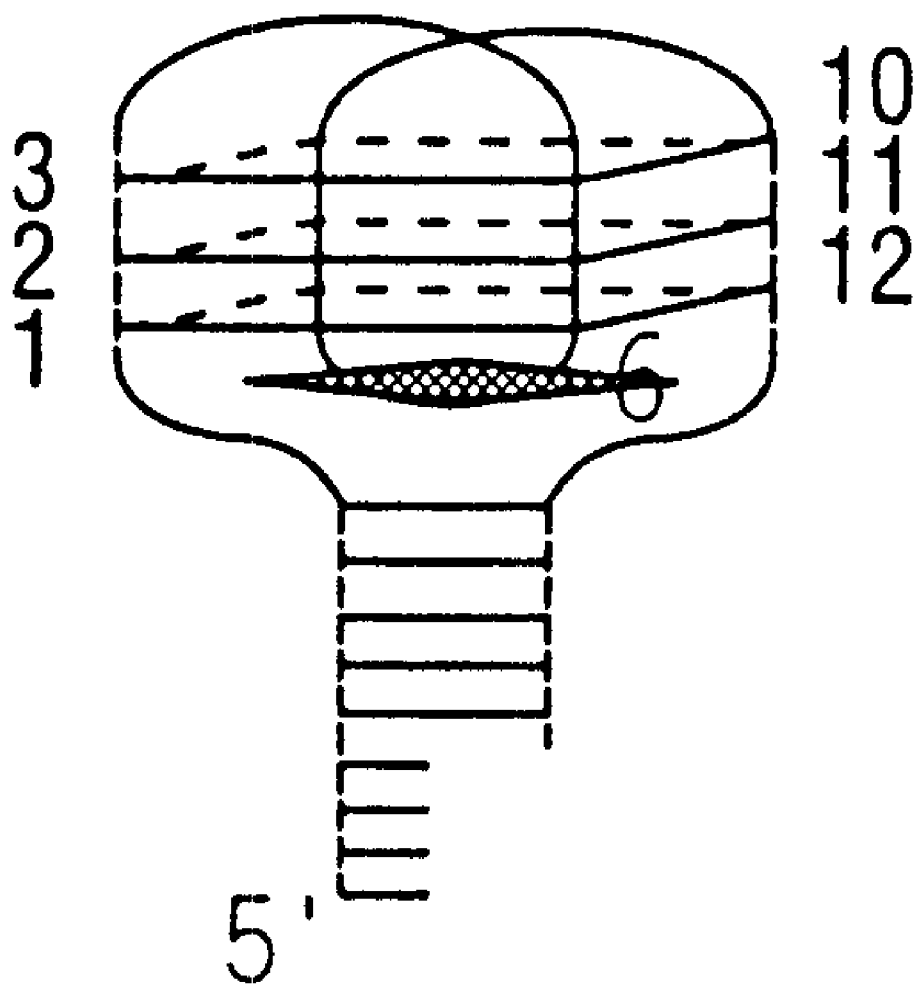
FIG. 6. Photocleavage of G4A DNA by TMPyP4 in K$^+$ buffer.

The G4A DNA was labeled with $^{32}$P at the 5' end and stored in 1×TE buffer at 3000 cpm/μl. For each photocleavage reaction, 10μ of DNA (~5 ng) was mixed with 10 μl of 200 mM KCl or 200 mM NaCl and boiled for 10 min before cooled down to room temperature. For the no porphyrin control samples, 10 μl of distilled water was added instead. The mixtures were transferred to a 96 well plate and added with 2 μl of 1 μM TMPyP4 aqueous solution. The samples were then exposed to 24 watts fluorescent daylight under a glass filter for different periods of time. Then the reactions were stopped with 100 μl of calf thymus DNA (0.1 μg/μl). After phenol-chloroform extraction, the samples were subjected to strand breakage treatment and ethanol precipitation. The DNA samples were loaded onto a 16% polyacrylamide gel for electrophoresis and visualized with Phosphorimager (from Molecular Dynamics, Inc.). A typical result for the photocleavage assay is shown in FIG. 6.

Example 6

Selection of G-Quadruplex Selective Ligand

The N,N'-bis(3 -morpholinopropyl)3,4,9,10-perylenetetracarboxilic acid diimide (KeTEL01) was synthesized from 3,4,9,10-perylenetetracarboxylic acid dianhydride and 3-morpholinopropylamine using a procedure analogous to that described above in example 5.3 for the synthesis of N,N'-bis(2-piperdinoethyl)-3,4,9,10-perylenetetracarboxylic acid diimide. A solution of KeTEL01 was prepared by dissolving 1 mg of KeTEL01 in 300 μL of 1 N HCl. To this solution was added 11 mL of a pH 7.0 buffer containing 20 mM sodium phosphate, 100 mM KCl, 1 mM EDTA, and 0.02% hydroxypropyl-β-cyclodextrin. Aliquots of this stock solution of KeTEL01 were transferred to 8 different quartz cuvettes and diluted into pH 7.0 mM sodium phosphate, 100 mM KCl, 1 mM EDTA buffer to afford solutions in which the concentration of KeTEL01 was 20 μM. To each of the cuvettes was added a solution of [d(TTAGGGT)]4 (SEQ ID No. 6) so that the final concentration of [d(TTAGGGT)]4 (SEQ ID No. 6) in each of the cuvettes was 0,4, 8, 12, 16, 20, 50, and 80 μM. These solutions were allowed to stand overnight in the dark, and the UV/VIS spectrum of each was determined. Pronounced, G-quadruplex concentration-dependent changes in the UV/VIS spectrum were noted at wavelengths 488 nm (~40% hypochromicity), 510 nm (~40% hyperchromicity) and 548 nm (~100% hyperchromicity). In a parallel study, changes in the UV/VIS spectrum of a 20 μM solution of KeTEL01 in a pH 7.0 20 mM phosphate buffer containing 100 mM KCl and 1 mM EDTA were determined upon the addition of 10 μM aliquots of a 3 mM (base pair) solution of calf thymus DNA. No changes in the UV/VIS spectrum of this solution were noted, indicating that KeTEL01 does not interact with double-stranded DNA.

Example 7

Kinetics of Interaction of KeTEL01 with G-Quadruplex DNA

A solution of 5 μM KeTEL01 in 20 mM phosphate buffer, 100 mM KCl, pH 7.0 was placed in a quartz cuvette and the UV/VIS spectrum determined. An aliquot of a solution of [d(TTAGGGT)]4 (SEQ ID No. 6) was added to the cuvette to afford a final concentration of 50 μM. The cuvette was quickly inverted several times and placed in the spectrophotometer. The absorption of the sample at 488 nm was continuously monitored for 3 hours, during which time, the absorption decreased in a multiexponential function. The time required for the absorption at 488 nm to reach one-half of its equilibrium value was 60 min.

Example 8

Telomerase Inhibition by UT-SK-02 (Diethylthiocarbocyanine Iodide)

Using the DOCK screening methods above, the carbocyanine group of compounds were identified as potential G-quadruplex interactive agents. A number of these compounds were assayed using the DNA Synthesis Arrest Assay described in example 5.4. Each compound was assayed at a concentration of 20 μM. The results of this study are summarized in Table 1 ahead:

TABLE 1

| Compound | Stop (F + P)$_{rel}$* | Stop (P/T)$_{rel}$** |
|---|---|---|
| IBT-129A | 68% | 91% |
| UT-SK-001 | 86% | 83% |
| UT-SK-002 | 88% | 139% |
| UT-SK-003 | 29% | 32% |
| UT-SK-004 | 71% | 88% |
| UT-SK-006 | 33% | 12% |

*Relative amount of both full-length and paused products.
**Relative ratio of the amount of paused products as compared to the total amount of products.

Of the compounds tested, only one, UT-SK-002 (diethylthiocarbocyanine iodide) demonstrated a specific interaction with G-quadruplex DNA, as indicated by a relative ratio of paused to total DNA product greater than 100% and a relative amount of DNA products, both paused and full length, that is close to 100%. In confirmatory tests, only this compound inhibited telomerase, with an inhibition of 10–35% at a concentration of 50 μM.

Example 9

Reduced Cellular Proliferation by Selected Compounds

The ability of these compounds to inhibit the proliferative capacity of human cancer cells was determined by a standard MTT assay. Briefly, cells were incubated for 72 hours in the presence of various concentrations of compound, and the cell viability was determined by monitoring the formation of a colored formazan salt of the tetrazolium salt 3-(4,5-dimethylthiazol-2-yl)-2,5-diphenyl tetrazolium bromide (MTT) by viable cells. KeTEL01 showed no cytotoxic effect up to the highest concentrations tested (100 μM), whereas KeTEL03 (N,N'-bis(2-dimethylaminoethyl)-3,4, 90,10-perylenetetracarboxylica acid diimide, see Example 1) showed good cytotoxicity in a variety of human cancer cell lines. Thus, KeTEL01, which is a selective G-quadruplex interactive agent, has no acute (72 hr) cytotoxic effect, but the structurally analogous KeTEL03, which does interact with double-stranded DNA as well as G-quadruplex, is cytotoxic under these assay conditions.

| | Cytotoxicity - IC$_{50}$ MTT | |
|---|---|---|
| Cell Lines | KeTEL01 | KeTEL03 |
| MCF-7 | >100 μM | 18.4 μM |
| BT-20 | >100 μM | 3.8 μM |
| PC-3 | >100 μM | 3.8 μM |
| Raji | >100 μM | 0.4 μM |

Example 10

DNA Oligonucleotides

The DNA primer extension sequence P18 (5'-TAATACGACTCACTATAG3') (SEQ ID No. 12) and the template sequences shown in Table 1 were synthesized using a PerSeptive Biosystems Expedite 8909 synthesizer and purified with denaturing polyacrylamide gels. The template DNA was diluted to 5 ng/μL and dispensed into small aliquots.

Example 11

DMS Methylation Protection Assay

The $^{32}$P-labeled PQ74 and HT4 templates were denatured by heating at 90° C. for 5 min and then cooled down to room temperature in 50 mM Tris-HCl buffer with or without 100 mM of K$^+$. One microliter of 1:4 ethanol-diluted DMS was added to 1 μg (300 μL) of annealed DNA. Aliquots were taken at time points as indicated in the figures, and modification reactions were stopped by adding ¼ volume of stop buffer containing 1 M of β-mercaptoethanol and 1.5 M of sodium acetate. The modification products were ethanol precipitated twice and treated with piperidine. After ethanol precipitation, the cleaved products were resolved on a 16% polyacrylamide gel.

Example 12

DNA Synthesis Arrest Assay

This assay is a modification of that described by Weitzmann and co-workers (Weitzmann et al., 1996). Briefly, primers (P18, 24 nM) labeled with [γ-$^{32}$P] were mixed with template DNA (12 nM)) in a Tris-HCl buffer (10 mM Tris, pH 8.0) containing K$^+$ (5 mM for the PQ74 template and 50 mM for the HT4 template) and denatured by heating at 90° C. for 5 min. After cooling down to room temperature, BSU-1051 was added at various concentrations and incubated at room temperature for 15 min. The primer extension reactions were initiated by adding dNTP (final concentration 100 μM), MgCl$_2$ (final concentration 3 μM), and Taq DNA polymerase (2.5 U/reaction, Boehringer Mannheim). For sequencing reactions, the TaqTrack Sequencing System (Promega, Madison, Wis.) was used. The sequencing reaction buffer was changed to 50 mM Tris-HCl, pH 9.0, 10 mM MgCl, and 50 mM K$^+$. The reactions were stopped by adding an equal volume of stop buffer (95% formamide, 10 mM EDTA, 10 mM NaOH, 0.1% xylene cyanol, 0.1% bromphenol blue). For the temperature-dependent studies, the ligand concentration was fixed and the primer extension reactions were carried out at the temperatures indicated in methods. The products were separated on a 12% polyacrylamide sequencing gel. The gels were then dried and visualized on a PhosphorImager (Molecular Dynamics model 445 S1).

Example 13

Results

The G-rich Regions of the PQ74 and HT-4 Templates Form Intermolecular G-quadruplex Structures in K+Buffer To determine the nature of the G-quadruplex structures formed by the template sequences used in this study (see Table 1), dimethylsulfate (DMS) was used to probe the accessibility of N7 of guanine in the DNA templates (Maxam and Gilbert, 1980). When the PQ74 template was methylated in 1×TE buffer, there was no apparent protection of any guanine N7. However, with the exception of the first guanine in each of the four TTGGGG (SEQ ID No. 7) repeats, all the guanines in the G-rich region of the PQ74 template are protected from reacting with DMS in 100 mM K+buffer, whereas guanines located outside the four repeats react strongly with DMS. This DMS protection pattern for the G-rich region of the PQ74 template in K+buffer suggests that only three guanines in each of the four TTGGGG (SEQ ID No. 7) repeats are involved in G-tetrad formation. This DMS reaction pattern is different from that observed previously by Henderson and co-workers (Henderson et al., 1990) with the d(TTGGGG)$_4$ (SEQ ID No. 7) G-quadruplex in which only the first guanine of the third repeat (corresponding to G9 in the PQ74 template) is hypersensitive to DMS methylation. On the basis of the results from the inventors' study, they propose a model for the G-quadruplex structure formed by the G-rich region of the PQ74 sequence consisting of d(TTGGGG)$_4$ (SEQ ID No. 7). In this model, the first guanine of the first repeat is located in the 5' overhang region and is therefore open to DMS methylation. However, the first guanines of the second, third, and fourth repeats (G5, G9, and G13, respectively) are located in the loop regions of the G-quadruplex. Although the N7 groups of these three loop guanines are not involved in hydrogen bonds, steric inaccessibility may protect them from DMS methylation. The DMS footprinting pattern shows that while they are partially protected from DMS methylation, this protection is less than that for the other guanines in the repeat.

The TTAGGG (SEQ ID No. 1) repeats in the G-rich region of the HT-4 template also showed high DMS methylation protection in K+buffer. In this particular case, all three guanines in each repeat were almost evenly protected from methylation, indicating that all of them are involved in G-tetrad formation. This DMS methylation pattern is consistent with the intramolecular G-quadruplex structure proposed by Patel and co-workers for the d[AG$_3$(T$_2$AG$_3$)$_3$] sequence based on NMR studies (Wang and Patel, 1993).

(ii) BSU-1051 Binds to G-quadruplex DNA and Blocks DNA Synthesis in a Concentration Dependent Manner Although it has been shown that G-quadruplex structures block primer extension by DNA polymerase in a K−dependent manner (Weitzmann et al., 1996), the inventors are unaware of any reports showing enhanced blockage by G-quadruplex —interactive agents. To determine if BSU-1051 binding to G-quadruplex enhances the block to DNA synthesis, primer extension reactions were carried out in the absence and presence of BSU-1051. Taq DNA polymerase primer extension on DNA templates containing four repeats of either TTGGGG (SEQ ID No. 7) (PQ74) or TTAGGG (SEQ ID No. 1) (HT4) in the presence of different concentrations of BSU-1051 at 55° C. were performed. In these studies, K+was added at low concentrations (5 mM of K+for the PQ74 template and 20 mM of K for the HT4 template) in order to prevent overwhelming polymerase pausing due to formation of highly stable G-quadruplex structures. In the absence of BSU-1051, there is only a slight pausing of the Taq DNA polymerase when it reaches the 3'-end of the G-rich site on the template DNA at 55° C. However, upon increasing the concentration of BSU-1051, enhanced pausing is observed at the same site as that seen with low K+concentrations. This suggests that BSU-1051 enhances the polymerase pausing by stabilizing the G-quadruplex structure formed in the K+buffer. At high BSU-1051 concentrations, the inventors not only observed enhanced pausing at the 3'-end of the G-quadruplex site but also increased premature termination resulting from nonspecific interactions between BSU-1051 and the single-stranded template DNA. At a BSU-1051 concentration of 100 μM, the primer extension is completely inhibited due presumably to nonspecific interactions between BSU-1051 and the single-and/or double-stranded DNA or between BSU-1051 and the polymerase itself. In addition to the primary pausing site at the beginning of the G-quadruplex site, two other secondary pausing sites at the second and third G-rich repeats are observed at high BSU-1051 concentrations. These pausings are probably induced by other structures formed by this G-rich sequence. Given the fact that secondary pausing beyond the first G-tetrad is not seen in the sequencing lanes that contain 50 mM K+, it is likely that these secondary pausings are caused by hairpin structures that are stabilized by BSU-1051 but not K+. This suggests that BSU-1051 has a relatively higher affinity for G-quadruplex DNA over other DNA secondary structures or single- and double-stranded DNA.

(iii) DNA Synthesis Arrest by the BSU-1051—G-quadruplex Complex Depends on the Stability of the G-quadruplex Structure To further evaluate the ability of BSU-1051 to stabilize G-quadruplex DNA, Taq DNA polymerase primer extension reactions were carried out at five different temperatures in the presence and absence of BSU-1051. In the absence of BSU-1051 polymerase pausing on the PQ74 template containing four repeats of TTGGGG (SEQ ID No. 7) is almost lost at around 65° C., which is presumably the melting point of the G-quadruplex structure formed by this G-rich region in the template DNA. On the other hand, in the presence of 20 μM BSU-1051, the G-quadruplex structure is further stabilized, and significant pausing is observed up to 74° C. In the HT4 template containing four repeats of TTAGGG (SEQ ID No. 1), in which the G-quadruplex structure formed is presumably less stable, pausing fades out at 55° C. in the absence of the ligand. However, in the presence of BSU-1051, pausing is observed up to 65° C. Thus, for both DNA sequences, ΔTm upon the addition of 20 μM BSU-1051 is about 20° C.

In order to confirm that the pausings seen result from the formation of a G-quadruplex structure on the template DNA, certain guanines in the templates were substituted with 7-deaza-dG. Since N7 of guanine is involved in hydrogen bonding in the formation of a G-quadruplex structure, substitution of guanine with 7-deaza-dG should preclude the formation of any G-quadruplex structure and allow for uninterrupted primer extension on the template by Taq DNA polymerase in the presence of either K+or BSU-1051. As shown in Table 1, two guanines in the TTAGGG (SEQ ID No. 1) repeat region of the HT4 template and four guanines in the TTGGGG (SEQ ID No. 7) repeat region of the PQ74 template were replaced with 7-deaza-dG. This change would allow the formation of no more than two intramolecular G-tetrads and should lead to destabilization of the intramolecular G-quadruplex structure. The primer extension results with these 7-deaza-dG substituted templates indicate that no significant pausing occurs in either template in the presence of up to 20 mM of $K^+$ or at BSU-1051 concentrations of up to 50 μM. This result provides strong support for the conclusion that BSU-1051 binds to and stabilizes intramolecular G-quadruplex DNA, leading to pronounced DNA synthesis arrest at the G-quadruplex site in the original G-rich templates.

Example 14

Discussion

G-rich sequences such as telomeric DNA and triplet DNA have been reported to form parallel or antiparallel G-quadruplex structures in the presence of monovalent cations such as $Na^+$ and $K^+$. Williamson and co-workers observed very strong intramolecular UV cross-linking for the sequence $d(TTGGGG)_4$ (SEQ ID No. 7) in a 50 mM $K^+$ buffer (Williamson et al., 1989). Their results indicate that this sequence forms an intramolecular structure. Using DMS methylation, the inventors conclude that four repeats of TTGGGG (SEQ ID No. 7) or TTAGGG (SEQ ID No. 1) within a non-G-rich sequence are capable of forming an intramolecular G-quadruplex structure in $K^+$ buffer. Furthermore, the DMS methylation results indicate that of the possible types of G-quadruplex structures that could be formed by $d(TTGGGG)_4$ (SEQ ID No. 7), a structure consisting of three G-tetrads is the predominant species in 100 mM of $K^+$ buffer. The proposed G-quadruplex structures formed by $d(TTGGGG)_4$ (SEQ ID No. 7) and $d(TTAGGG)_4$ (SEQ ID No. 7) repeats have diagonal loops, but alternative intramolecular G-quadruplex structures formed by foldover hairpins consisting of three G-tetrads are also possible (Williamson, 1994; Wang and Patel, 1995; Wang and Patel, 1994). However, the inventors could not differentiate between these two different types of intramolecular G-quadruplex structures by the DMS methylation pattern alone.

G-rich sequences that are capable of forming G-quadruplexes in vitro can be found in telomeric sequences (Blackburn, 1991; Sundquist and Klug, 1989; Kang et al., 1992), immunoglobulin switch regions (Sen and Gilbert, 1988), the insulin gene (Hommond-Kosack et al., 1993), the control region of the retinoblastoma susceptibility gene (Murchie and Lilley, 1992), the promoter region of c-myc gene (Simonsson et al., 1998), fragile X syndrome triplet repeats (Nadel et al., 1995; Fry and Loeb, 1994), and HIV-1 RNA (Awang and Sen, 1993). It has been suggested by Sen and Gilbert that telomeric DNA sequences may associate to initiate the alignment of four sister chromatids by forming parallel guanine quadruplexes (Sen and Gilbert, 1990). Furthermore, the discovery of G-quadruplex—forming sequences in the promoter region of certain genes suggests that G-quadruplex structures may play a role in the transcription regulation of these genes. Another possible role of G-quadruplex DNA is the regulation of telomere length, since a telomeric overhang that forms a G-quadruplex structure would not be a good substrate for telomerase (Henderson and Blackburn, 1989; Zahler et al., 1991). The inventors recently have demonstrated that BSU-1051 inhibits primer extension by telomerase only when the substrate (telomeric DNA) reaches four or more repeats in length (Sun et al., 1997). In this report, the inventors show that BSU-1051 is able to bind to and stabilize the intramolecular G-quadruplex structure formed by four telomeric repeats. Thus, it is reasonable to postulate that BSU-1051 inhibits telomerase by interacting with its substrate (G-quadruplex—forming telomeric repeats) rather than telomerase itself. If G-quadruplex structures play important roles in other biological processes, then G-quadruplex—interactive compounds such as those described here, which stabilize these structures, may have a variety of biological effects. A series of 2,6-diamidoanthraquinones, including BSU-1051, has been reported to moderate conventional cytotoxicity in a range of tumor cells (Collier and Neidle, 1988; Agbandje et al., 1992) and to inhibit human telomerase (Perry et al., 1998). The G-quadruplex binding property of those compounds provides a possible mechanism for their action, although other mechanisms involving targeting of duplex DNA are also likely.

The inventors have recently proposed a model for a perylene—G-quadruplex complex based on NMR evidence (Fedoroff et al., 1998). By analogy with this structure and that proposed for a $TMPyP_4$—G-quadruplex structure (Wheelhouse et al., 1998), it seems most likely that the binding site of the BSU-1051 is external to the lower G-tetrad and within the diagonal loop (see FIG. 5).

The block of DNA synthesis by G-quadruplex structures is not polymerase specific. Woodford and co-workers showed that the $K^+$ dependent DNA synthesis arrest by G-quadruplex structures is similar for various polymerases (Woodword et al., 1994). The inventors have found that the BSU-1051—induced DNA synthesis arrest pattern is virtually identical when Taq DNA polymerase, *E. coli* DNA polymerase I (Klenow fragment), or AMV reverse transcriptase is used. Given the fact that many G-rich DNA sequences are capable of forming G-quadruplexes in-vitro (particularly some cancer related genes and sequences such as c-myc and telomeres), G-quadruplexs are targets for anticancer chemotherapy. The DNA synthesis stop assay described in this report provides a simple and rapid method for the identification of G-quadruplex—interactive agents as lead compounds. This polymerase stop assay also allows an internal comparison for the relative binding of potential G-quadruplex—interactive compounds with single and double-stranded DNA targets. This is an important comparison that may provide clues as to the relative cytotoxicity of these compounds.

The inventors have successfully used the present assay in the identification and characterization of other G-quadruplex—interactive compounds that are also telomerase inhibitors (Fedoroff et al., 1998; Wheelhouse et al., 1998). This assay can be used to identify other G-quadruplex-interactive compounds with potential clinical utility.

REFERENCES

The following references, to the extent that they provide exemplary procedural or other details supplementary to those set forth herein, are specifically incorporated herein by reference.

Agbandje, Jenkins, McKerma, Reszka, Neidle, "Anthracene-9,10-diones as potential anticancer agents. Synthesis, DNA binding, and biological studies on a series of 2,6-disubstituted derivatives," Med. Chem., 35:1418–1429, 1992.

Allshire, Gosden, Cross, Cranston, Rout, Sugawara, Szostak, Fantes, Hastie, "Telomeric repeat from *T. ther-* mophilia cross hybridizes with human telomeres," Nature, 332:656–659, 1988.

Blackburn, "Structure and function of telomeres," Nature, 350:569–573, 1991.

Blackburn, Greider, Eds., In: Telomeres," Cold Spring Harbor Press, New York, 1995.

Broccoli, Young, de Lange, "Telomerase activity in normal and malignant hematopoietic cells," Proc. Natl. Acad. Sci. U.S.A., 92:9082–9086, 1994.

Chen, Kuntz, Shafer, "Spectroscopic recognition of guanine dimeric hairpin quadruplexes by a carbocyanine dye," Proc. Natl. Acad. Sci. U.S.A., 93:2635–2639, 1996.

Collier and Neidle, "Synthesis, molecular modeling, DNA binding, and antitumor properties of some substituted amidoanthraquinones," Med. Chem., 31:847–857, 1988.

Collins and Greider, "Tetrapymena telomerase catalyzes nucleolytic cleavage and nonprocessive elongation," Genes Dev., 7:1364–1376, 1993.

Counter, Avilion, LeFeuvre, Stewart, Greider, Harley, Bacchetti, "Telomere shortening associated with chromosome instability is arrested in immortal cells which express telomerase activity," EMBO J., 11:1921–1929, 1992.

Feng, Funk, Wang, Weinrich, Avilion, Chin, Adams, Chang, Allsopp, Yu, Le, West, Harley, Andrews, Greider, Villeponteau, "The RNA component of human telomerase," Science, 269:1236–1241, 1995.

Fox, Polucci, Jenkins, Neidle, "A molecular anchor for stabilizing triple-helical DNA," Proc. Nail. Acad Sci. USA., 92:7887–7891, 1995.

Haq, Ladbury, Chowdry, Jenkins, "Molecular anchoring of duplex and triplex DNA by disubstituted anthracene-9/10-diones: calorimetric, UV melting, and competition dialysis studies," J. Am. Chem. Soc., 118:10693–10701, 1996.

Harley, Futcher, Greider, "Telomeres shorten during aging of human fibroblasts," Nature, 345:458460, 1990.

Harley, Kim, Prowse, Weinrich, Hirsch, West, Bacchetti, Hirte, Counter, Greider, Wright, Shay, "Telomerase, Cell Immortality, and Cancer," Cold Spring Harbor Syrup. Quant Biol., 59:307–315, 1994.

Hiyama, Hiyama, Ishioka, Yamakido, Inai, Gazdar, Piatyszek, Shay, "Telomerase activity in small-cell and non-small-cell lung cancers," Natl. Cancer Inst., 87:895–902, 1995a.

Hiyama, Hiyama, Yokoyama, Matsuura, Piatyszek, Shay, "Correlating telomerase activity levels with human neuroblastoma outcomes," Nature Medicine, 1:249–255, 1995a.

Kang, Zhang, Ratlift, Moyzis, Rich, "Crystal structure of four-stranded Oxytricha telomeric DNA," Nature, 356:126–131, 1992.

Kim, Piatyszek, Prowse, Harley, West, Ho, Coviello, Wright, Weinrich, Shay, "Specific association of human telomerase activity with immortal cells and cancer," Science, 266:2011–2015, 1994.

Laughlan, Murchie, Norman, Moore, Moody, Lilley, Luisi, "The high-resolution crystal structure of a parallel-stranded guanine tetraplex," Science, 265:520–524, 1994.

Norton, Piatyszek, Woodring, Shay, Corey, "Inhibition of human telomerase activity by peptide nucleic adds," Nature Biotechnology, 14:615–619, 1996.

Parkinson, "Do telomerase antagonists represent a novel anti-cancer strategy?" Brit. J. Cancer, 73:14, 1996.

Rhyu, "Telomeres, telomerase, and immortality," Natl. Cancer Inst., 87:884–894, 1995.

Salazar, Thompson, Kerwin, Hurley, "Thermally induced DNA:RNA hybrid to G-quadruplex transitions: possible implications for telomere synthesis by telomerase," Biochemistry, 35:16110–16115, 1996.

Tanious, Jenkins, Neidle, Wilson, "Substituent position dictates the intercalative DNA-binding mode for anthracene-9,10-dione antitumor drugs," Biochemistry, 31:11632–11640,1992.

Wang and Patel, "Guanine residues in $d(T_2AG_3)$ and $d(T_2G_4)$ form parallel-stranded potassium cation stabilized G-quadruplexes with anti glycosialic torsion angles in solution, Biochemistry, 31:8112–8119, 1992.

Weitzmann, N. M., Woodford, K., Usdin, K. (1996), J. Biol. Chem., 271, 20958–20964)

Zahler, Williamson, Cech, Prescott, "Inhibition of telomerase by G-quartet DNA structures," Nature, 350:718–720, 1991.

What is claimed is:

1. A method of identifying a telomerase inhibitor comprising:
   a) contacting a compound with DNA G-quadruplex; and
   b) determining the melting point of the DNA G-quadruplex wherein a compound exhibiting an increase in melting point of said quadruplex, relative to unbound DNA G-quadruplex, is indicated to inhibit telomerase activity.

* * * * *

UNITED STATES PATENT AND TRADEMARK OFFICE
CERTIFICATE OF CORRECTION

PATENT NO. : 6,623,930 B2
DATED : September 23, 2003
INVENTOR(S) : Kerwin et al.

It is certified that error appears in the above-identified patent and that said Letters Patent is hereby corrected as shown below:

<u>Column 35,</u>
Line 55, delete "(3-qualdruplex" and insert -- G-quarduplex -- therefor.

Signed and Sealed this

Twenty-fifth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,623,930 B2
APPLICATION NO. : 09/940173
DATED : September 23, 2003
INVENTOR(S) : Sean M. Kerwin et al.

It is certified that error appears in the above-identified patent and that said Letters Patent is hereby corrected as shown below:

In column 1, lines 13-17, delete
"The government may own rights in the present invention pursuant to contract number U19CA-67760-02, and contract number NCDDG, CA67760 from the National Cancer Institute, and contract number CA4975 1 and contract number CA77000 from the National Institutes of Health." and insert
--This invention was made with government support under contract No. U19CA67760-02 and National Cooperative Drug Discovery Grant No. CA67760 from the National Cancer Institute, and contract numbers CA49751 and CA77000 from the National Institutes of Health. The government has certain rights in the invention.--
therefor.

Signed and Sealed this

Thirty-first Day of March, 2009

JOHN DOLL
*Acting Director of the United States Patent and Trademark Office*